United States Patent
Guery et al.

(10) Patent No.: US 11,883,446 B2
(45) Date of Patent: Jan. 30, 2024

(54) PROBIOTICS FOR USE IN THE PREVENTION OR TREATMENT OF ILLNESS AND/OR SYMPTOMS ASSOCIATED WITH CORONAVIRUSES

(71) Applicant: DUPONT NUTRITION BIOSCIENCES APS, Copenhagen (DK)

(72) Inventors: Sebastien Guery, Munich (DE); Markus Lehtinen, Vantaa (FI); Sinikka Anneli Latvala, Helsinki (FI); Liisa Lehtoranta, Sundsberg (FI); Bryan-James Zabel, Madison, WI (US); Wesley William Morovic, Edgerton, WI (US); Charles Budinoff, Oregon, WI (US); Scott D. Power, Woodside, CA (US)

(73) Assignee: DUPONT NUTRITION BIOSCIENCES APS, Lyngby (DK)

(*) Notice: Subject to any disclaimer, the term of this patent is extended or adjusted under 35 U.S.C. 154(b) by 11 days.

(21) Appl. No.: 17/711,081

(22) Filed: Apr. 1, 2022

(65) Prior Publication Data

US 2022/0370519 A1    Nov. 24, 2022

Related U.S. Application Data

(63) Continuation of application No. 17/240,433, filed on Apr. 26, 2021, now Pat. No. 11,318,174.
(Continued)

(30) Foreign Application Priority Data

Jul. 31, 2020    (EP) .................................... 20188807

(51) Int. Cl.
*A61K 35/745* (2015.01)
*A61P 31/14* (2006.01)
*A61K 35/744* (2015.01)

(52) U.S. Cl.
CPC .......... *A61K 35/745* (2013.01); *A61K 35/744* (2013.01); *A61P 31/14* (2018.01)

(58) Field of Classification Search
CPC .. A61K 35/745; A61K 35/744; A61K 35/741; A61K 45/06; A61K 2035/115; A61P 31/14; A23K 10/18; A23L 33/135
See application file for complete search history.

(56) References Cited

U.S. PATENT DOCUMENTS

| | | |
|---|---|---|
| 2009/0196921 A1 | 8/2009 | Ebel et al. |
| 2012/0114608 A1 | 5/2012 | Ebel et al. |
| 2012/0128644 A1 | 5/2012 | Hillman et al. |

FOREIGN PATENT DOCUMENTS

| | | |
|---|---|---|
| KR | 101104397 B1 | 1/2021 |
| WO | 2008053444 A2 | 5/2008 |

(Continued)

OTHER PUBLICATIONS

Baud et al., (Front. Public Health, May 8, 2020 Sec. Infectious Diseases—Surveillance, Prevention and Treatment vol. 8—2020. Published May 8, 2020. (Year: 2020).*

(Continued)

*Primary Examiner* — Jana A Hines

(57) ABSTRACT

This invention relates to bacterial strains, compositions comprising bacterial strains as well as methods and uses of said strains and compositions for preventing or treating illness and/or symptoms associated with a coronavirus in a subject in need thereof.

3 Claims, 19 Drawing Sheets

Related U.S. Application Data

(60) Provisional application No. 63/140,097, filed on Jan. 21, 2021, provisional application No. 63/107,878, filed on Oct. 30, 2020, provisional application No. 63/050,009, filed on Jul. 9, 2020.

(56) References Cited

FOREIGN PATENT DOCUMENTS

| WO | 2016120320 A1 | 8/2016 | |
|---|---|---|---|
| WO | WO-2016120320 A1 * | 8/2016 | ............ A23L 33/135 |

OTHER PUBLICATIONS

European Search Report issued in European appl. No. EP20188807, dated Feb. 2, 2021, 4 pages.

Bessell et al., Commercial bacteria stimulate antitumor responses via T cell cross-negativity; JCI Insight, Apr. 2020 p(8); e135597, 20 pages.

Grifoni et al., A Sequence Homology and Bioinformatic Approach Can Predict Canditate Targets for Immune Responses to SARS-CoV-2; Cell Hose Microbe; Apr. 2020; 27(4):671-80 e2.

Netea et al., Defining trained immunity and its role in health and disease, Nature Reviews Immunology, vol. 20,June eo20, p. 375-388.

Popova et al., Beneficial effects of probiotics in upper respiratory tract infections and their mechanical actions to antagonize pathogens, Journal of Applied Microbiology, Wiley-Blackwell Publishing Ltd, vol. 113, No. 6, Dec. 1, 2012.

Sahoo et al., 2019 Novel Coronavirus, Ann Ibd. Pg. Med, vol. 17, No. 2, 2019, pp. 108-110.

* cited by examiner

PROBIOTICS FOR USE IN THE PREVENTION OR TREATMENT OF ILLNESS AND/OR SYMPTOMS ASSOCIATED WITH CORONAVIRUSES

CROSS-REFERENCE TO RELATED APPLICATIONS

This application is a continuation of U.S. patent application Ser. No. 17/240,433, filed Apr. 26, 2021, now U.S. Pat. No. 11,318,174, which claims priority to U.S. Provisional Patent Application No. 63/050,009, filed Jul. 9, 2020, European Patent Application No. 20188807.0, filed Jul. 31, 2020, U.S. Provisional Patent Application No. 63/107,878, filed Oct. 30, 2020, and U.S. Provisional Patent Application No. 63/140,097, filed Jan. 21, 2021, the disclosure of each which is incorporated by reference herein in its entirety

FIELD OF THE INVENTION

This invention relates to new uses of bacterial strains and compositions comprising said bacterial strains for preventing or treating illness and/or symptoms associated with coronaviruses. The invention also relates to methods for preventing or treating illness and/or symptoms associated with coronaviruses comprising administering such strains or compositions to a subject in need thereof. In particular, the coronavirus is SARS-CoV-2.

BACKGROUND

Coronaviruses (Coronaviridae) have been long recognized as one of the causative agents of common cold and respiratory infections in humans and a variety of respiratory illnesses in animals. However, it has only been in the 21st century that coronavirus variants have emerged as pandemic pathogens. In 2002, the SARS-CoV virus emerged and in short order demonstrated the high infectivity characteristic of modern strains. The appearance of MERS coronavirus on the Arabian Peninsula followed a similar trajectory.

Since the outbreak of SARS (Severe Acute Respiratory Syndrome) coronavirus 2 (SARS-CoV-2), causing coronavirus disease (COVID-19), the world has experienced a fast spread of this highly infectious virus leading to a global pandemic. While approximately 15-20% of the tested cases are asymptomatic, most of the affected patients have mild symptoms that includes fever (83-98% of symptomatic cases), cough (59-82% of symptomatic cases), shortness of breath (19-55% of symptomatic cases) and muscle ache (11-44% of symptomatic cases). However, in some patients, this disease will progress to a more severe state that will develop around 8 days after the infection has occurred. The main symptoms go from dyspnea to respiratory distress with 3-29% of patients needing admission to Intensive Care Units (ICUs). The disease course then may lead to acute respiratory distress syndrome (ARDS) (17-29% of patients hospitalized), severe sepsis with shock and in some cases multiple organ dysfunction within one week. Last, it has been estimated that the global mortality rate of infected patients is approximately 5-7%.

The challenges presented by this virus are various: its high contagiousness combined with a fair share of asymptomatic carriers allow for the infection to spread rapidly and undetected amongst the population. This leads to a fast increase of cases in all countries infected which has put huge pressure on existing healthcare infrastructures leading to high death tolls.

Furthermore, unlike the other coronaviruses, this variant has retained its virulence even though as an RNA virus, it is expected to undergo mutation at a relatively high frequency. In addition, the lack of animal models of the disease has hindered the ability of vaccine developers to demonstrate efficacy and the rapid spread has called for employing shortcuts to get to human trials without a wealth of animal data.

Consequently, all infected countries, except a handful of them, went into extensive lockdowns, limiting social gathering, restricting travels and forcing most businesses to limit activities to its bare minimum and in most cases to close. Such measures have triggered the "economics of stoppage" creating a global recession with devastating consequences for the global population.

Over the past few months, government, non-governmental organizations (NGOs) and private firms have refocused some of their efforts to find treatments against COVID-19. The most common approaches can be clustered into three main categories: i) passive immunity/neutralizing antibodies, ii) vaccines and iii) drug repurposing.

With regards to the approaches above, one product has been approved to treat severe cases of COVID-19 (the small molecule drug Remdesivir). However, recently published clinical data do not show a strong benefit vs. placebo. On 12th of May 2020, 1368 clinical trials against COVID-19 were registered in clinicaltrials.gov

OBJECT OF THE INVENTION

In order to overcome the challenges presented by the current outbreak of SARS-CoV-2 and other coronavirus caused/associated respiratory illness or disease, the inventors believe that a key to a successful outcome for preventing or treating the population against coronavirus associated severe respiratory syndrome disease in general and COVID-19 specifically will be to provide a product that would: (i) enable the immune system to (a) secrete antibodies against SARS-CoV-2, (b) stimulate pre-existing SARS-CoV-2 crossreactive T cells, and (3) develop novel SARS-CoV-2 cross-reactive T cells using bacterial strains having microbial cross reactive antigens (mCRAGs) and/or (ii) activate the immune system to stimulate anti-viral immunity before infection with SARS-CoV2. The present inventors believe that this approach, i.e., the use of either mCRAGs or the activation of the immune system by probiotic strain intervention can be used alone and/or in addition to other approaches being considered currently by other research groups, like vaccines.

It is therefore an object of the present invention to provide a method, as well as bacterial strains and compositions comprising bacterial strains, to be used in preventing or treating illness and/or symptoms associated with coronaviruses in a subject in need thereof. In particular, it is the object of the present invention to provide bacterial strains to be used in preventing or treating illness and/or symptoms associated with a SARS-CoV-2 virus in a subject in need thereof.

SUMMARY OF THE INVENTION

In one aspect, the invention relates to a bacterial strain of the genus *Bifidobacterium* or a mixture thereof for use in preventing or treating illness and/or symptoms associated with coronaviruses in a subject in need thereof.

In another aspect, the present invention relates to a bacterial strain of the genus *Lacticaseibacillus* or a mixture thereof for use in preventing or treating illness and/or symptoms associated with coronaviruses in a subject in need thereof.

In another aspect, the present invention relates to a bacterial strain of the genus *Ligilactobacillus* or a mixture thereof for use in preventing or treating illness and/or symptoms associated with coronaviruses in a subject in need thereof.

In a further aspect, the present invention relates to a bacterial strain of the genus *Lactobacillus* or a mixture thereof for use in preventing or treating illness and/or symptoms associated with coronaviruses in a subject in need thereof.

In a further aspect, the present invention relates to a bacterial strain of the genus *Limosilactobacillus* or a mixture thereof for use in preventing or treating illness and/or symptoms associated with coronaviruses in a subject in need thereof.

In a further aspect, the present invention relates to a bacterial strain of the genus *Lactococcus* or a mixture thereof for use in preventing or treating illness and/or symptoms associated with coronaviruses in a subject in need thereof.

In another aspect, the present invention relates to a bacterial strain of the genus *Streptococcus* or a mixture thereof for use in preventing or treating illness and/or symptoms associated with coronaviruses in a subject in need thereof.

In a further aspect, the present invention relates to a composition comprising one or more bacterial strains chosen from the genera *Bifidobacterium, Lacticaseibacillus, Ligilactobacillus, Lactobacillus, Limosilactobacillus, Lactococcus* and *Streptococcus*.

In yet a further aspect, the present invention relates to a method of treating or preventing illness and/or symptoms associated with coronaviruses in a subject in need thereof, said method comprising administering a bacterial strain of the genus *Bifidobacterium* or a mixture thereof to said subject.

In yet a further aspect, the present invention a method of treating or preventing illness and/or symptoms associated with coronaviruses in a subject in need thereof, said method comprising administering a bacterial strain of the genus *Lacticaseibacillus* or a mixture thereof to said subject.

In another aspect, the present invention relates to method of treating or preventing illness and/or symptoms associated with coronaviruses in a subject in need thereof, said method comprising administering a bacterial strain of the genus *Ligilactobacillus* or a mixture thereof to said subject.

In another aspect, the present invention relates to a method of treating or preventing illness and/or symptoms associated with coronaviruses in a subject in need thereof, said method comprising administering a bacterial strain of the genus *Lactobacillus* or a mixture thereof to said subject.

In a further aspect, the present invention relates to method of treating or preventing illness and/or symptoms associated with coronaviruses in a subject in need thereof, said method comprising administering a bacterial strain of the genus *Limosilactobacillus* or a mixture thereof to said subject.

In a further aspect, the present invention relates to a method of treating or preventing illness and/or symptoms associated with coronaviruses in a subject in need thereof, said method comprising administering a bacterial strain of the genus *Lactococcus* or a mixture thereof to said subject.

In another aspect, the present invention relates to a method of treating or preventing illness and/or symptoms associated with coronaviruses in a subject in need thereof, said method comprising administering a bacterial strain of the genus *Streptococcus* or a mixture thereof to said subject.

In yet a further aspect, the present invention relates to a use of a bacterial strain of the genus *Bifidobacterium* or a mixture thereof for preventing or treating illness and/or symptoms associated with coronaviruses in a subject in need thereof.

In yet a further aspect, the present invention relates to a use of a bacterial strain of the genus *Lacticaseibacillus* or a mixture thereof for preventing or treating illness and/or symptoms associated with coronaviruses in a subject in need thereof.

In another aspect, the present invention relates to a use of a bacterial strain of the genus *Ligilactobacillus* or a mixture thereof for preventing or treating illness and/or symptoms associated with coronaviruses in a subject in need thereof.

In another aspect, the present invention relates to a use of a bacterial strain of the genus *Lactobacillus* or a mixture thereof for preventing or treating illness and/or symptoms associated with coronaviruses in a subject in need thereof.

In another aspect, the present invention relates to a use of a bacterial strain of the genus *Limosilactobacillus* or a mixture thereof for preventing or treating illness and/or symptoms associated with coronaviruses in a subject in need thereof.

In a further aspect, the present invention relates to a use of a bacterial strain of the genus *Lactococcus* or a mixture thereof for preventing or treating illness and/or symptoms associated with coronaviruses in a subject in need thereof.

In a further aspect, the present invention relates to a use of a bacterial strain of the genus *Lactococcus* or a mixture thereof for preventing or treating illness and/or symptoms associated with coronaviruses in a subject in need thereof.

In another aspect, the present invention relates to a use of a bacterial strain of the genus *Streptococcus* or a mixture thereof for preventing or treating illness and/or symptoms associated with coronaviruses in a subject in need thereof.

Advantages

It is surprisingly found by the present inventors that the use of bacterial strains of the genera *Bifidobacterium, Lacticaseibacillus, Ligilactobacillus, Lactobacillus, Limosilactobacillus, Lactococcus* or *Streptococcus* or compositions comprising said bacterial strains can be used for preventing or treating illness and/or symptoms associated with coronaviruses, in particular SARS-CoV-2 virus, in a subject in need thereof.

DETAILED DISCLOSURE OF THE INVENTION

Figure 1A:
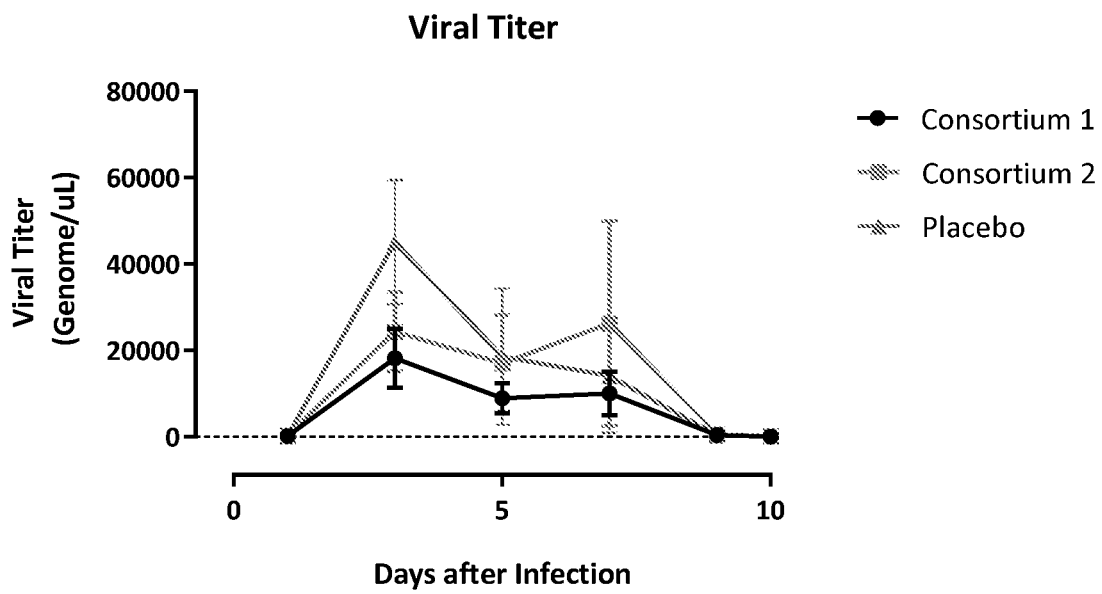
FIG. 1A is a chart showing nasal wash viral titers in SARS CoV-2-infected ferrets up 10 ten days post infection.

The detailed aspects of this invention are set out below. In part some of the detailed aspects are discussed in separate sections. This is for ease of reference and is in no way limiting. All of the embodiments described below are equally applicable to all aspects of the present invention unless the context specifically dictates otherwise.

Mucosal IgA is broadly cross-reactive against microbiota and helps maintain microbiota homeostasis with the host. Without being bound to theory, by ingesting probiotic bacterial strains that have homologous epitopes with coronaviruses, including SARS-CoV-2, surface polypeptides (mainly S protein), it could be possible to induce cross-reactive IgA antibodies that could reduce the risk of infection by cross-reacting with SARS-CoV-2 or other coronavirus virions at the mucosal surfaces. Mucosal IgA antibodies also function in transporting viral particles from host side of the epithelium to microbiota side via polymeric Ig receptor expressed in epithelial cells.

To produce antigen specific reactions and novel antibody production, probiotics strains should induce T-cell dependent reactions in the gut/mucosa. If consumed as powder, these antibodies may also be produced in the mucosa of respiratory tract.

The antigen specific T-cell dependent reactions are driven in secondary lymphoid tissues (lymph nodes/peyer's patches) by (i) antigen presenting cells that ingest probiotics and display cross-reactive peptides on MHC-II/MHC-I molecules on their surface, (ii) CD4 T-cells recognizing the peptide:MHC-II complexes, (iii) antigen specific CD8 T-cells activated by CD4 T-cells, and (iv) B-cells activated by B-cell receptor binding the pathogen and displaying the peptide in MHC-II and (v) CD4 T-cells activated by the peptide from the same bacterium by antigen presenting cell.

T-cell dependent IgA production is driven by TGF-β (IgA class switching), and expansion/differentiation of B-cells by IL-5, IL-6, IL-10, and IL-21—secreted by CD4 T-cells. This is basically a tolerogenic Treg/barrier protecting Th17 response to microbiota that is induced by dendritic cells secreting IL-6, IL-10, IL-23, TGF-β.

Ingestion of probiotics induces IgA responses in the intestine. It has been shown that some plasma B-cells (Ab producing cells) travel to other mucosal sites (~10%), for example, the respiratory tract (~1-2%), to add to existing plasma cell/IgA pool.

CD8 memory cells are important in eradication of virus infected cells and driving anti-viral immunity. It has been shown that healthy humans have memory CD8 T-cells against commensal microbes. Further it was shown that the bacterial strain *Bifidobacterium breve* harboring a cross-reactive peptide to tumor neoantigen was able to influence tumor reactive CD8 T-cells (Bessell C A, Isser A, Havel J J, Lee S, Bell D R, Hickey J W, et al. Commensal bacteria stimulate antitumor responses via T cell cross-reactivity; JCI Insight; 2020; 5(8)), suggesting that microbiota could also influence antigen specific memory CD8 T-cell pool against pathogens. CD8 responses are typically initiated by IL-12/IFN-γ and Th1 type dendritic/CD4 T-cells. Thus, probiotics could influence pre-existing coronavirus cross-reactive memory CD8 T cells, but also memory CD4 T-cells.

Probiotic bacterial strain consumption can also influence existing plasma cell activation and IgA pool. If there is existing cross-reactive IgA against SARS-CoV-2, probiotics could support total IgA production by T-cell independent mechanisms. Commensal microbiota/probiotics induce total IgA production (antigen independent) in the intestine, and potentially may have an influence in extra-intestinal IgA production as well. For example, short chain fatty acids and induction of TGF-β (IgA class-switching), IL-6, retinoic acid, BAFF and APRIL from epithelia drive the IgA production.)

Probiotic supplementation against cold and flu has been studied in clinical studies over 20 years. Several meta-analyses of clinical studies have shown that probiotics in general could be effective in reducing the risk and duration of the respiratory tract infections. However, there are strain specific differences between probiotics on immune stimulation and beneficial effects against respiratory tract infections. Research on *B. lactis* Bl-04, *L. acidophilus* NCFM, and *B. lactis* Bi-07 and other studies in the literature indicate that probiotics function by "training" innate immune responses, i.e, function by priming the immune system before the viral infection. Studies have shown increased expression of interferons and innate immune cytokines prior to reducing the viral load or the risk of infections by roughly 20%.

Although all viruses have different pathogenesis and life cycle, they still induce similar anti-viral immune responses—characterized by NK-cell, ILC1, cytotoxic T lymphocyte, Th1 responses, and IgG antibody production as well as production of interferons alpha, beta, gamma, and lambda, activation of the inflammasome and Th1 associated cytokines, such as IL-12, and IP-10. Thus, stimulation of the innate immune system against SARS-CoV-2 could be effective also against other coronaviruses Viruses evade these immune responses by for example producing molecules that inhibit interferon production and cellular immunity. It has been reported that in SARS-CoV-2 infections interferon responses are delayed.

Probiotics, like *Lactobacillus acidophilus* NCFM, have been shown to induce specific pathways associated with anti-viral immunity like interferon beta, and to increase expression of receptors (TLR3) that detect viral RNA. Further, NCFM reduced the incidence of cold symptoms in children aged 3-5 years. It also drives IL-12 production in vitro. Without being bound to theory, it is believed that by selecting a bacterial strain or a consortium of one or more optimized probiotics that drive/stimulate anti-viral responses the risk of SARS-CoV-2 infection and severe COVID-19 disease can be reduced and the duration and course of the disease shortened with potential reduction in the total symptom load.

It seems that oral ingestion and intestinal exposure is enough to drive innate immune changes at other mucosal sites, such as the respiratory tract, potentially by travelling lymphocytes and influencing lympho/myelopoiesis, but also potentially via the gut-brain axis and microbial metabolites in the circulation system.

Probiotic effects have been tested on dendritic cells and the type of cytokine profile they produce has been measured. By selecting high IL-12/IFN-γ and low IL-10/TGF-β producers of the immune cells, the best probiotic and combination of probiotics against SARS-CoV-2, and also against other coronaviruses and viral respiratory pathogens, was chosen.

Therefore, in some non-limiting embodiments, any of the microbes or microbial consortia disclosed herein can be used to modulate (i.e. increase or decrease) expression of one or more cytokines (e.g. inflammatory cytokines) such as, without limitation, IL-12, IL-10, IL-1β, TNFα, IL-8, IL-6. In further non-limiting embodiments, any of the microbes or microbial consortia disclosed herein can be used to modulate (i.e. increase or decrease) expression of one or more chemokines such as, without limitation, CCL2, CCL5, and/or CXCL10. In yet further embodiments, any of the microbes or microbial consortia disclosed herein can be used to modulate (i.e. increase or decrease) expression of one or more interferons such as, without limitation, IFNα, IFNL1, and IFNγ. In addition, in some non-limiting embodiments, any of the microbes or microbial consortia disclosed herein can be used to modulate (i.e. increase or decrease) expression of one or more of the ACE2 receptor and TLR8.

In some embodiments, any of the microbes or microbial consortia disclosed herein can be used to modulate (i.e. increase or decrease) expression of one or more cytokines (e.g. inflammatory cytokines) such as, without limitation, IL-12, IL-10, IL-1β, TNFα, IL-8, IL-6 by any of about 5%, 10%, 15%, 20%, 25%, 30%, 35%, 40%, 45%, 50%, 55%, 60%, 65%, 70%, 75%, 80%, 85%, 90%, 95%, or 100%, inclusive of all values falling within these percentages, when administered to a subject compared to modulation of these one or more cytokines in subjects that have not been administered one of the microbes or microbial consortia disclosed herein. In some embodiments the consortium comprises *Bifidobacterium longum* subsp. *infantis* strain Bi-26; *Bifidobacterium animalis* subsp. *lactis* strain Bl-04; *Lacticaseibacillus paracasei* strain Lpc-37; *Lacticaseibacillus rhamnosus* strain Lr-32 and/or strain GG and *Ligilactobacillus salivarius* strain Ls-33. In other embodiments, the consortium comprises *Bifidobacterium animalis* subsp. *lactis* strain Bi-07; *Lactobacillus acidophilus* strain NCFM; *Limosilactobacillus fermentum* strain SBS-1; *Lactococcus lactis* strain Ll-23 and/or *Streptococcus thermophilus* strain St-21.

In another embodiment, any of the microbes or microbial consortia disclosed herein can be used to modulate (i.e. increase or decrease) expression of one or more chemokines such as, without limitation, CCL2, CCL5, and/or CXCL10 by any of about 5%, 10%, 15%, 20%, 25%, 30%, 35%, 40%, 45%, 50%, 55%, 60%, 65%, 70%, 75%, 80%, 85%, 90%, 95%, or 100%, inclusive of all values falling within these percentages, when administered to a subject compared to modulation of these one or more chemokines in subjects that have not been administered one of the microbes or microbial consortia disclosed herein. In some embodiments the consortium comprises *Bifidobacterium longum* subsp. *infantis* strain Bi-26; *Bifidobacterium animalis* subsp. *lactis* strain Bl-04; *Lacticaseibacillus paracasei* strain Lpc-37; *Lacticaseibacillus rhamnosus* strain Lr-32 and/or strain GG and *Ligilactobacillus salivarius* strain Ls-33. In other embodiments, the consortium comprises *Bifidobacterium animalis* subsp. *lactis* strain Bi-07; *Lactobacillus acidophilus* strain NCFM; *Limosilactobacillus fermentum* strain SBS-1; *Lactococcus lactis* strain Ll-23 and/or *Streptococcus thermophilus* strain St-21.

In another embodiment, any of the microbes or microbial consortia disclosed herein can be used to modulate (i.e. increase or decrease) expression of one or more interferons such as, without limitation, IFNα, IFNL1, and IFNγ by any of about 5%, 10%, 15%, 20%, 25%, 30%, 35%, 40%, 45%, 50%, 55%, 60%, 65%, 70%, 75%, 80%, 85%, 90%, 95%, or 100%, inclusive of all values falling within these percentages, when administered to a subject compared to modulation of these one or more interferons in subjects that have not been administered one of the microbes or microbial consortia disclosed herein. In some embodiments the consortium comprises *Bifidobacterium longum* subsp. *infantis* strain Bi-26; *Bifidobacterium animalis* subsp. *lactis* strain Bl-04; *Lacticaseibacillus paracasei* strain Lpc-37; *Lacticaseibacillus rhamnosus* strain Lr-32 and/or strain GG and *Ligilactobacillus salivarius* strain Ls-33. In other embodiments, the consortium comprises *Bifidobacterium animalis* subsp. *lactis* strain Bi-07; *Lactobacillus acidophilus* strain NCFM; *Limosilactobacillus fermentum* strain SBS-1; *Lactococcus lactis* strain Ll-23 and/or *Streptococcus thermophilus* strain St-21.

In further embodiments, any of the microbes or microbial consortia disclosed herein can be used to modulate (i.e. increase or decrease) expression of one or more receptor proteins such as, without limitation, ACE2 or TLR8, by any of about 5%, 10%, 15%, 20%, 25%, 30%, 35%, 40%, 45%, 50%, 55%, 60%, 65%, 70%, 75%, 80%, 85%, 90%, 95%, or 100%, inclusive of all values falling within these percentages, when administered to a subject compared to modulation of these one or more receptor proteins in subjects that have not been administered one of the microbes or microbial consortia disclosed herein. In some embodiments the consortium comprises *Bifidobacterium longum* subsp. *infantis* strain Bi-26; *Bifidobacterium animalis* subsp. *lactis* strain Bl-04; *Lacticaseibacillus paracasei* strain Lpc-37; *Lacticaseibacillus rhamnosus* strain Lr-32 and/or strain GG and Ligilactobacillus *salivarius* strain Ls-33. In other embodiments, the consortium comprises *Bifidobacterium animalis* subsp. *lactis* strain Bi-07; *Lactobacillus acidophilus* strain NCFM; *Limosilactobacillus fermentum* strain SBS-1; *Lactococcus lactis* strain Ll-23 and/or *Streptococcus thermophilus* strain St-21.

Macrophages are phagocytic cells that are present in almost all tissues of the body where they function as sentinels of the immune system and first line responders to viral infections. Tissue macrophages originate from circulating monocytes, which after homing into peripheral tissues differentiate into tissue-specific macrophages. Dendritic cells function in the interface of innate and adaptive immune responses and are involved in pathogen recognition, shaping of T-cell activation, antibody response, and directing the cells towards Th1, Th2, Th17 or Treg polarization. Exposure of immune cells to bacteria, their products or food and feed components can trigger the expression of inflammatory mediators such as cytokines and chemokines to initiate immune responses or maintain tolerance. These responses induced within in vitro cell culture models are useful in predicting the effects of different food and feed ingredients in vivo.

Bacteria

The bacterial strains of the present invention are selected from bacterial strains of the genera *Bifidobacterium, Lacticaseibacillus*, Ligilactobacillus, *Lactobacillus, Limosilactobacillus, Lactococcus* and *Streptococcus*. Preferably the bacterial strains of the present invention are of the species *Bifidobacterium longum* subsp. *infantis, Bifidobacterium animalis* subsp. *lactis, Lacticaseibacillus* paracasei, *Lacticaseibacillus rhamnosus, Ligilactobacillus salivarius, Lactobacillus acidophilus, Limosilactobacillus fermentum, Lactococcus lactis* and *Streptococcus* thermophilus. In particular, the bacterial strains are chosen from the strains Bi-26, Bl-04, Bi-07, Lpc-37, Lr-32, GG, Ls-33, NCFM, SBS-1, Ll-23 and St-21. The strains can be used individually or in combination and, for example in food products, food ingredients, dietary supplements or in pharmaceutical acceptable compositions or formulations. The strains can be in a consortium containing one or more of Bi-26, Bl-04, Lpc-37, Lr-32, and/or Ls-33. The strains can also be in a consortium containing one or more of Bi-07, NCFM, SBS-1, Ll-23, and/or St-21.

Preferably the bacterial strains to be used in the present invention are bacterial strains which are generally recognized as safe and, which are preferably GRAS approved. Generally recognized as safe (GRAS) is an American Food and Drug Administration (FDA) designation that a chemical or substance added to food is considered safe by experts, and so is exempted from the usual Federal Food, Drug, and Cosmetic Act (FFDCA) food additive tolerance requirements.

In one embodiment, the present invention relates to a bacterial strain of the genus *Bifidobacterium* or a mixture thereof for use in preventing or treating illness and/or symptoms associated with coronaviruses in a subject in need thereof.

In one embodiment, the term "subject", as used herein, means a mammal, including for example livestock (for example cattle, horses, pigs, and sheep) and humans. In one embodiment the subject is a human. In one embodiment the subject is female. In one embodiment the subject is male. In another embodiment, the subject is a dog (such as a member of the genus *Canis*) or a cat (such as a member of the genera *Felis* or *Panthera*). In another embodiment, the subject is poultry, for example Chicken, turkeys, ducks and geese.

In particular, the strain of the genus *Bifidobacterium* is a strain of the species *Bifidobacterium longum* subsp. *infantis* and a strain of the species *Bifidobacterium animalis* subsp. *lactis*. More particularly, the strain of the species *Bifidobacterium longum* subsp. *infantis* is strain Bi-26 and the strains of the species *Bifidobacterium* animalis subsp. *lactis* are strains Bl-04 and Bi-07.

In another embodiment, the present invention relates to a bacterial strain of the genus *Lacticaseibacillus* or a mixture thereof for use in preventing or treating illness and/or symptoms associated with coronaviruses in a subject in need thereof.

In particular, the strain of the genus *Lacticaseibacillus* is a strain of the species *Lacticaseibacillus paracasei* and a strain of the species *Lacticaseibacillus rhamnosus*. More particularly, the strain of the species *Lacticaseibacillus paracasei* is strain Lpc-37 and the strain of the species *Lacticaseibacillus rhamnosus* are strains Lr-32 and/or GG.

In another embodiment, the present invention relates to bacterial strain of the genus *Ligilactobacillus* or a mixture thereof for use in preventing or treating illness and/or symptoms associated with coronaviruses in a subject in need thereof.

In particular, the strain of the genus *Ligilactobacillus* is a strain of the species *Ligilactobacillus salivarius* and, more particularly, the strain is strain Ls-33.

In another embodiment, the present invention relates to a bacterial strain of the genus *Lactobacillus* or a mixture thereof for use in preventing or treating illness and/or symptoms associated with coronaviruses in a subject in need thereof. More particularly, the strain of the genus *Lactobacillus* is a strain of the species *Lactobacillus acidophilus*. More particularly, the strain of the species *Lactobacillus acidophilus* is strain NCFM.

In a further embodiment, the present invention relates to a bacterial strain of the genus *Limosilactobacillus* or a mixture thereof for use in preventing or treating illness and/or symptoms associated with coronaviruses in a subject in need thereof. In particular, strain of the genus *Limosilactobacillus* is a strain of the species *Limosilactobacillus fermentum* and, more particularly, the strain is strain SBS-1.

In a further embodiment, the present invention relates to a bacterial strain of the genus *Lactococcus* or a mixture thereof for use in preventing or treating illness and/or symptoms associated with coronaviruses in a subject in need thereof. In particular, the strain of the genus *Lactococcus* is a strain of the species *Lactococcus lactis* and more particularly, the strain of the species *Lactococcus lactis* is strain Ll-23.

In another embodiment, the present invention relates to a bacterial strain of the genus *Streptococcus* or a mixture thereof for use in preventing or treating illness and/or symptoms associated with coronaviruses in a subject in need thereof. In particular, the strain of the genus *Streptococcus* is a strain of the species *Streptococcus thermophilus*, and more particularly strain St-21.

The bacterial strains of the present invention are all commercially available from DuPont Nutrition Biosciences ApS.

The bacterial strains were also deposited by DuPont Nutrition Biosciences ApS, of Langebrogade 1, DK-1411 Copenhagen K, Denmark, in accordance with the Budapest Treaty at the Leibniz-Institut Deutsche Sammlung von Mikroorganismen and Zellkulturen GmbH (DSMZ), Inhoffenstrasse 7B, 38124 Braunschweig, Germany, where they are recorded under the following registration numbers:

a) Strain Bi-26 (DGCC11473); deposited on 23 Feb. 2021 under registration number DSM33525.
b) Strain Bl-04 (DGC2908); deposited on 19 May 2020 under registration number DSM33525.
c) Strain Lpc-37 (DGCC4715); deposited on 9 Feb. 2009 under registration number DSM22266.
d) Strain Lr-32 (DGCC9913); deposited on 15 Jan. 2009 under registration number DSM22193.
e) Strain Ls-33 (DGCC9868); deposited on 23 Feb. 2021 under registration number DSM33831.
f) Strain Bi-07 (DGCC12895); deposited on 19 May 2020 under registration number DSM33526.

g) Strain NCFM (DGCC8698); deposited on 15 Mar. 2021 under registration number DSM33840.

h) Strain SBS-1 (DGCC1925); deposited on 29 Jul. 2015 under registration number DSM32105.

i) Strain Ll-23 (DGCC8656); deposited on 23 Feb. 2021 under registration number DSM33830.

j) Strain St-21 (DGCC7693); deposited on 23 Feb. 2021 under registration number DSM33829.

Coronaviruses can cause various illnesses or diseases in mammals and birds. In humans, these viruses can cause respiratory tract infections that can range from mild to lethal. Mild illnesses include some cases of the common cold while more lethal virus can cause severe acute respiratory syndrome (SARS) (SARS-CoV), Middle East respiratory syndrome (MERS) (MERS-CoV) and acute respiratory distress syndrome (ARDS) in the case of COVID-19 (SARS-CoV-2). In many patients, the respiratory distress is followed by severe sepsis with shock and in some cases multiple organ dysfunction within one week, resulting in a mortality rate of infected patients of approximately 5-7%.

Additionally, even after recovery from COVID-19, a significant number of individuals continue to be afflicted with symptoms. In the United States, these individuals have been called post-COVID "long haulers." In the United Kingdom, they are said to be suffering from "long COVID." Published studies (Carfi et al., *JAMA*, 2020 Aug. 11; 324 (6):603-605 doi: 10.1001/jama.2020.12603) and surveys conducted by patient groups indicate that 50% to 80% of patients continue to have bothersome symptoms three months after the onset of COVID-19 even after tests no longer detect virus in their body (Komaroff, 2020, Harvard Health Blog, The tragedy of the post-COVID "long haulers," posted Oct. 15, 2020). The most common symptoms are fatigue, body aches, shortness of breath, difficulty concentrating, inability to exercise, headache, and difficulty sleeping.

In one embodiment, the illness caused by coronaviruses is a respiratory illness. More particularly, the respiratory illness is acute respiratory distress syndrome (ARDS).

In another embodiment, the respiratory illness is pneumonia.

According to the World Health Organization (WHO), the most common symptoms of COVID-19 are fever, dry cough and tiredness. Less common symptoms include aches and pains, sore throat, diarrhoea, conjunctivitis, headache loss of taste or smell, a rash on skin, or discolouration of fingers or toes. Serious symptoms include difficulty breathing or shortness of breath, chest pain or pressure and loss of speech or movement.

In one embodiment, the symptoms caused by coronaviruses are one or more of cough, fever, shortness of breath or difficulty breathing (dyspnea), fatigue, muscle or body aches, nausea or vomiting, diarrhea, loss or change of sense of smell (anosmia), and loss or change of sense of taste (ageusia). In another embodiment, one or more symptoms (including, without limitation, fatigue, body aches, shortness of breath, difficulty concentrating, inability to exercise, headache, and difficulty sleeping) continue for any of about 1, 2, 3, 4, 5, 6, 7, 8, 9, or more months after the initial onset of COVID-19 and/or after virus is no longer detectable a subject's body.

In another embodiment, the prevention and/or treatment of the illness and/or symptoms associated with coronaviruses is achieved by stimulation of the immune system in the subject when in contact with one or more of the bacterial strains object of the present invention.

Coronaviruses are a group of related RNA viruses and these include 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

In one embodiment, the present invention relates to any coronavirus belonging to the family Coronaviridae. The coronavirus are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface.

In one embodiment, the coronavirus according to the present invention is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

In a particular embodiment of the present invention, the coronavirus is SARS-CoV-2 virus.

Some people are at high risk from coronavirus (clinically extremely vulnerable). These include people who have had an organ transplant; people who are having chemotherapy or antibody treatment for cancer, including immunotherapy; people who are having an intense course of radiotherapy (radical radiotherapy) for lung cancer; people who are having targeted cancer treatments that can affect the immune system (such as protein kinase inhibitors or PARP inhibitors); people who have blood or bone marrow cancer (such as leukaemia, lymphoma or myeloma); people who have had a recent bone marrow or stem cell transplant, or are still taking immunosuppressant medicine; people who have a severe lung condition (such as cystic fibrosis, severe asthma or severe COPD); people who have a medical condition that means they have a very high risk of getting infections, such as SCID or sickle cell; people who are taking medicine that makes them much more likely to get infections, such as high doses of steroids or immunosuppressant medicine; and people who have a serious heart condition and are pregnant.

Some people are at moderate risk from coronavirus (clinically vulnerable). These include people who are 70 or older; people who have a lung condition that's not severe (such as asthma, COPD, emphysema or bronchitis); people who have heart disease (such as heart failure); people who have diabetes (type I or type II diabetes); people who have chronic kidney disease; people who have liver disease (such as hepatitis); people who have a condition affecting the brain or nerves (such as Parkinson's disease, motor neurone disease, multiple sclerosis or cerebral palsy); people who have a condition that means they have a high risk of getting infections; people who are taking medicine that can affect the immune system (such as low doses of steroids); people who are very obese (a BMI of 40 or above); people who are pregnant.

There are also other factors that can affect your risk, such as being male, living in a care home (such as a nursing home or long-term care facility) or being an inmate in a prison or jail.

In one embodiment, the present invention relates to a subject who has one or more pre-existing conditions selected from the group consisting of obesity, type II diabetes, chronic lung disease or moderate to severe asthma, heart conditions, immunocompromised, chronic kidney disease and liver disease.

In a further embodiment, the present invention relates to a subject who is 65 years of age or older and/or is a resident in a nursing home or long-term care facility or jail or prison.

The invention further provides a mutant, a variant and/or a progeny of the bacterial strains Bi-26, Bl-04, Bi-07, Lpc-37, Lr-32, GG, Ls-33, NCFM, SBS-1, Ll-23 and St-21.

As used herein, the term "mutant" refers to any microorganism resulting from modification of the strains Bi-26, Bl-04, Bi-07, Lpc-37, Lr-32, GG, Ls-33, NCFM, SBS-1, Ll-23 and St-21. For example, a mutant may be a microorganism resulting from genetically modifying these strains.

As used herein, the term "variant" refers to a naturally occurring microorganism which is derived from the strains Bi-26, Bl-04, Bi-07, Lpc-37, Lr-32, GG, Ls-33, NCFM, SBS-1, Ll-23 and St-21. For example, a variant may be a microorganism resulting from adaption to a particular environment or cell culture conditions.

As used herein, the term "progeny" means any microorganism resulting from the reproduction or multiplication of any one of the strains Bi-26, Bl-04, Bi-07, Lpc-37, Lr-32, GG, Ls-33, NCFM, SBS-1, Ll-23 and St-21. Therefore, "progeny" means any direct descendant of any one of these strains. As such, the progeny strain may itself be identified as the same strain as the parent strain (i.e. strains Bi-26, Bl-04, Bi-07, Lpc-37, Lr-32, GG, Ls-33, NCFM, SBS-1, Ll-23 and St-21). It will be apparent to one skilled in the art that due to the process of asexual reproduction, a progeny strain will be genetically virtually identical to the parent strain. Accordingly, in one embodiment, the progeny may be genetically identical to the parent strain and may be considered to be a "clone" of the parent strain. Alternatively, the progeny may be substantially genetically identical to the parent strain.

The mutant, variant or progeny may have at least 90, 95, 98, 99, 99.5 or 99.9% sequence identity over the entire length of the bacterial genome with their parent strain. Furthermore, the mutant, variant or progeny will retain the same phenotype as the parent strain, for example the mutant, variant or progeny may demonstrate the same or equivalent effect on preventing or treating illness and/or symptoms associated with coronaviruses in a subject in need thereof.

For the purpose of the present invention, any mutant, variant and/or progeny of the bacterial strains Bi-26, Bl-04, Bi-07, Lpc-37, Lr-32, GG, Ls-33, NCFM, SBS-1, Ll-23 and St-21 are considered to be the same as strains Bi-26, Bl-04, Bi-07, Lpc-37, Lr-32, GG, Ls-33, NCFM, SBS-1, Ll-23 and St-21, respectively.

Compositions

While it is possible to administer *Bifidobacteria, Lacticaseibacillus, Ligilactobacillus, Lactobacillus, Limosilactobacillus, Lactococcus* or *Streptococcus* alone according to the present invention (i.e., without any support, diluent or excipient), the *Bifidobacteria, Lacticaseibacillus, Ligilactobacillus, Lactobacillus, Limosilactobacillus, Lactococcus* or *Streptococcus* are typically administered on or in a support as part of a product, in particular as a component or at least as one of the components of a composition, a dietary supplement, a nutritional supplement, a food product or a pharmaceutical acceptable composition or formulation. These products typically contain additional components well known to those skilled in the art.

In one embodiment, the present invention relates to a composition comprising one or more bacterial strains chosen from the genera *Bifidobacterium, Lacticaseibacillus, Ligilactobacillus, Lactobacillus, Limosilactobacillus, Lactococcus* and *Streptococcus*. In a particular embodiment, the composition comprises one or more bacterial strain chosen from the species *Bifidobacterium longum* subsp. *infantis, Bifidobacterium animalis* subsp. *lactis, Lacticaseibacillus paracasei, Lacticaseibacillus rhamnosus, Ligilactobacillus salivarius, Lactobacillus acidophilus, Limosilactobacillus fermentum, Lactococcus lactis* and *Streptococcus thermophilus*.

In a particular embodiment, the present invention relates to a composition comprising one or more of the bacterial strains chosen from strain Bi-26, strain Bl-04, strain Lpc-37; strain Lr-32 and strain Ls-33.

In a particular embodiment, the present invention relates to a composition comprising one or more of the bacterial strains chosen from strain Bi-26, strain Bl-04, strain Lpc-37; strain Lr-32, strain Ls-33 and/or strain GG.

In another particular embodiment, the composition according to the present invention comprises one or more of the bacterial strains chosen from strain Bi-07, strain NCFM, strain SBS-1, strain Ll-23 and strain St-21.

In another particular embodiment, the composition according to the present invention comprises one or more of the bacterial strains chosen from strain Bi-07, strain NCFM, strain SBS-1, strain Ll-23, strain St-21 and/or strain GG.

The composition as described in the present invention is used in or for preventing or treating illnesses and/or symptoms associated with coronaviruses in a subject in need thereof. The coronavirus can be one of the coronaviruses selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus, or any other coronavirus belonging to the family Coronaviridae or any new variants of these viruses. In particular, the coronavirus is SARS-CoV-2 virus.

The subject being treated with the composition has or can have one or more pre-existing conditions selected from the group consisting of obesity, type II diabetes, chronic lung disease or moderate to severe asthma, heart conditions, immunocompromised, chronic kidney disease and liver disease.

In one embodiment, the subject is 65 years of age or older and/or is a resident in a nursing home or long-term care facility or jail or prison.

In one particular embodiment, the illness associated with the coronavirus is a respiratory illness, and more particularly, acute respiratory distress syndrome (ARDS) and or pneumonia.

In another embodiment, the symptoms associated with the coronavirus are one or more of shortness of breath or difficulty breathing (dyspnea), fatigue, muscle or body aches, nausea or vomiting, diarrhea, cough, fever, loss or change of sense of smell (anosmia) and loss or change of sense of taste (ageusia).

The composition as described in the present invention, when used and administered to the subject achieves the prevention or treatment by stimulating the immune system of the subject.

The composition can be presented in different forms, such as a food product, food ingredient, a dietary supplement or a pharmaceutical acceptable composition or formulation.

Another embodiment, the present invention relates to a method of treating or preventing illness and/or symptoms associated with coronaviruses in a subject in need thereof, said method comprising administering a bacterial strain of the genus *Bifidobacterium* or a mixture thereof to said subject. In particular, the strains are of the species *Bifidobacterium longum* subsp. *Infantis* and/or *Bifidobacterium* animalis subsp. *lactis*. More particularly, the strains are strain Bi-26, strain Bl-04 or/and strain Bi-07.

In another embodiment, the present invention relates to a method of treating or preventing illness and/or symptoms associated with coronaviruses in a subject in need thereof, comprising administering a bacterial strain of the genus *Lacticaseibacillus* or a mixture thereof to said subject. In particular, the strains are of the species *Lacticaseibacillus paracasei* and/or *Lacticaseibacillus rhamnosus*. More particularly, the strains are strain Lpc-37, Lr-32 and/or strain GG.

In a further embodiment, the present invention relates to a method of treating or preventing illness and/or symptoms associated with coronaviruses in a subject in need thereof, the method comprising administering a bacterial strain of the genus *Ligilactobacillus* or a mixture thereof to said subject. In particular, the strains are of the species *Ligilactobacillus salivarius* and/or *Ligilactobacillus salivarius*. More particularly, the strain is Ls-33.

In a further embodiment, the present invention relates to a method of treating or preventing illness and/or symptoms associated with coronaviruses in a subject in need thereof, the method comprising administering a bacterial strain of the genus *Lactobacillus* or a mixture thereof to said subject. In particular, the strains are of the species *Lactobacillus acidophilus*, more particularly the bacterial strain is strain NCFM.

In another embodiment, the present invention also relates to a method of treating or preventing illness and/or symptoms associated with coronaviruses in a subject in need thereof, comprising administering a bacterial strain of the genus *Limosilactobacillus* or a mixture thereof to said subject. In particular, the strains are of the species *Limosilactobacillus fermentum*. More particularly, the strain of the species *Limosilactobacillus fermentum* is strain SBS-1.

In a further embodiment, the present invention relates to a method of treating or preventing illness and/or symptoms associated with coronaviruses in a subject in need thereof, comprising administering a bacterial strain of the genus *Lactococcus* or a mixture thereof to said subject. In particular, the strain is of the species *Lactococcus lactis* and, more particularly, it is strain Ll-23.

In a further embodiment, the present invention relates to a method of treating or preventing illness and/or symptoms associated with coronaviruses in a subject in need thereof, comprising administering a bacterial strain of the genus *Streptococcus* or a mixture thereof to said subject. In particular, the strains are of the species *Streptococcus thermophilus* and, more particularly it is strain St-21.

Dosage

The bacterial strains used in accordance with the present invention may be present from $10^6$ to $10^{14}$ CFU of bacteria/g of support, and more particularly from $10^8$ to $10^{12}$ CFU of bacteria/g of support, preferably $10^9$ to $10^{12}$ CFU/g of support.

Suitably, the bacterial strains used in accordance with the present invention, such as strains Bi-26, Bl-04, Bi-07, Lpc-37, Lr-32, GG, Ls-33, NCFM, SBS-1, Ll-23 and St-21, may be administered at a dosage of from about $10^6$ to about $10^{14}$ CFU of microorganism/dose, preferably about $10^8$ to about $10^{12}$ CFU of microorganism/dose and more preferably from about $10^9$ to about $10^{11}$ CFU of microorganism/dose. By the term "per dose" it is meant that this amount of microorganism is provided to a subject either per day or per intake, preferably per day. For example, if the microorganisms are to be administered in a food product, for example in a yoghurt, then the yoghurt will preferably contain from about $10^8$ to $10^{12}$ CFU of the microorganism. Alternatively, however, this amount of microorganism may be split into multiple administrations each consisting of a smaller amount of microbial loading—so long as the overall amount of microorganism received by the subject in any specific time, for instance each 24-hour period, is from about $10^6$ to about $10^{12}$ CFU of microorganism, preferably $10^8$ to about $10^{12}$ CFU of microorganism and more preferably from about $10^9$ to about $10^{11}$ CFU of microorganism.

In accordance with the present invention an effective amount of at least one strain of a microorganism may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, preferably the bacterial strains, such as strains Bi-26, Bl-04, Bi-07, Lpc-37, Lr-32, GG, Ls-33, NCFM, SBS-1, Ll-23 and St-21, may be administered at a dosage of from about $10^6$ to about $10^{14}$ CFU of microorganism/day, preferably about $10^8$ to about $10^{12}$ CFU of microorganism/day, more preferably about $10^9$ to about $10^{11}$ CFU of microorganism/day. Hence, the effective amount in this embodiment may be from about $10^6$ to about $10^{14}$ CFU of microorganism/day, preferably about $10^8$ to about $10^{12}$ CFU of microorganism/day, more preferably about $10^9$ to about $10^{11}$ CFU of microorganism/day.

By "support" is meant a composition, a food product, a food ingredient, a dietary supplement or a pharmaceutically acceptable composition. CFU stands for "colony-forming units".

Food Product

In one embodiment, the bacterial strains are used according to the invention in a food product, such as a food supplement, a drink or a powder based on milk. Here, the term "food" is used in a broad sense and covers food for humans as well as food for animals (i.e. a feed). In a preferred aspect, the food is for human consumption.

The food may be in the form of a solution or as a solid, depending on the use and/or the mode of application and/or the mode of administration.

When used as, or in the preparation of, a food, such as functional food, the bacteria of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the bacteria of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, vegetable milk, acidified soy/juice beverage, aseptic/retorted chocolate drink, bar mixes, beverage powders, calcium fortified soy/plain and chocolate milk, calcium fortified coffee bever Advantageously, where the product is a food product, the bacterial strains should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment age.

Food Ingredients

Compositions of the present invention may take the form of a food ingredient and/or feed ingredient.

As used herein the term "food ingredient" or "feed ingredient" includes a composition which is or can be added to functional foods or foodstuffs as a nutritional and/or health supplement for humans and animals.

The food ingredient may be in the form of a liquid, suspension or solid, depending on the use and/or the mode of application and/or the mode of administration Dietary Supplements The compositions of the present invention may take the form of dietary supplements or may themselves be used in combination with dietary supplements, also referred to herein as food supplements.

The term "dietary supplement" as used herein refers to a product intended for ingestion that contains a "dietary ingredient" intended to add nutritional value or health benefits to (supplement) the diet. A "dietary ingredient" may include (but is not limited to) one, or any combination, of the following substances: bacteria, a probiotic (e.g. probiotic bacteria), a vitamin, a mineral, a herb or other botanical, an amino acid, a dietary substance for use by people to supplement the diet by increasing the total dietary intake, a concentrate, metabolite, constituent, or extract.

Dietary supplements may be found in many forms such as tablets, capsules, soft gels, gel caps, liquids, or powders. Some dietary supplements can help ensure an adequate dietary intake of essential nutrients; others may help prevent or treat diseases.

Medical Food

Compositions of the present invention may take the form of medical foods.

By "medical food" it is meant a food which is formulated to be consumed or administered with or without the supervision of a physician and which is intended for a specific dietary management or condition for which distinctive nutritional requirements, based on recognized scientific principles, are established by medical evaluation.

Pharmaceutical Composition

The bacteria of the present invention may be used as—or in the preparation of—a pharmaceutical composition or formulation. Here, the term "pharmaceutical" is used in a broad sense—and covers pharmaceuticals for humans as well as pharmaceuticals for animals (i.e. veterinary applications).

In a preferred embodiment, the pharmaceutical acceptable composition is a medicament.

The pharmaceutical composition can be for therapeutic purposes—which may be curative or palliative or preventative in nature. The pharmaceutical composition may even be for diagnostic purposes.

In a preferred embodiment of the present invention, the medicament is for oral administration.

A pharmaceutically acceptable composition or support may be for example a formulation or support in the form of creams, foams, gels, lotions, and ointments of compressed tablets, tablets, capsules, ointments, suppositories or drinkable solutions.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

Yeasts in general have been shown to be adjuvants in oral administration. *Yarrowia*, in particular, has been shown to drive the correct IL-12/Th1/interferon gamma path as well as inducing IL-27 leading to CD8 Cytotoxoc T-Lymphocyte synthesis/activation. It also appears to induce IL-17 production by the Th17 cell subset, normally involved in innate immunity of the gut epithelium including wall integrity.

Therefore, in a particular embodiment, the adjuvant is a yeast and, more particularly, *yarrowia*.

The pharmaceutical may be in the form of a solution or as a solid—depending on the use and/or the mode of application and/or the mode of administration.

The bacterial strains of the present invention may be used as pharmaceutical ingredients. Here, the composition may be the sole active component, or it may be at least one of a number (i.e. 2 or more) of active components.

The pharmaceutical ingredient may be in the form of a solution or as a solid—depending on the use and/or the mode of application and/or the mode of administration.

The bacterial strains may be used according to the present invention in any suitable form—whether when alone or when present in a combination with other components or ingredients. Likewise, combinations comprising the bacteria of the present invention and other components and/or ingredients (i.e. ingredients—such as food ingredients, functional food ingredients or pharmaceutical ingredients) may be used in any suitable form.

The bacterial strains may be used according to the present invention in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the bacteria of the present invention are used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid 30 monoglycerides and diglycerides, petroethrai fatty acid esters, hydroxymethylcellulose, polyvinylpyrrolidone, and the like.

Preferred excipients for the forms include lactose, starch, a cellulose, milk sugar or high molecular weight polyethylene glycols.

For aqueous suspensions and/or elixirs, the bacteria of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

In one aspect, the bacteria according to the present invention may be administered in an aerosol, for example by way of a nasal spray, for instance for administration to the respiratory tract.

Prebiotics

In one embodiment, the bacterial strains and compositions of the present invention may further be combined or comprise one or more fibres and/or prebiotics.

Prebiotics are defined as a substrate that is selectively utilized by host microorganisms conferring a health benefit. These are generally ingredients that beneficially affect the health of the host by selectively stimulating the growth and/or activity of one or a limited number of bacteria, and thus improve host health. The prebiotic can be applied to oral route, but it can be also applied to other microbioally colonized sites. Typically, prebiotics are carbohydrates (such as oligosaccharides), but the definition does not preclude non-carbohydrates, such as polyphenols, or polyunsaturated fatty acids or other ingredients that can be utilized selectively by a limited number of bacteria to confer a health benefit. The most prevalent forms of prebiotics are nutritionally classed as soluble fibres. To some extent, many forms of dietary fibres exhibit some level of prebiotic effect.

In one embodiment, a prebiotic is a selectively fermented ingredient that allows specific changes, both in the composition and/or activity in the gastrointestinal or skin microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 10 g/day, preferably 2 to 9 g/day, more preferably 3 to 8 g/day. In another embodiment, the prebiotic may be used according to the present invention in an amount of 5 to 50 g/day, preferably 5 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), polydextrose 10 (i.e. Litesse®), lactitol, L-Arabinose, D-Xylose, L-Rhamnose, D-Mannose, L-Fucose, inositol, sorbitol, mannitol, xylitol, fructose, carrageenan, alginate, microcrystalline cellulose (MCC), betaine, lactosucrose, soybean oligosaccharides, isomaltulose (Palatinose™), isomalto-oligosaccharides, gluco-oligosaccharides, xylooligosaccharides, manno-oligosaccharides, beta-glucans, cellobiose, raffinose, gentiobiose, melibiose, xylobiose, cyciodextrins, isomaltose, trehalose, stachyose, panose, pullulan, verbascose, galactomannans, (human) milk oligosaccharides and all forms of resistant starches.

The combination of one or more of the bacterial strains according to the present invention and one or more fibres and/or prebiotics according to the present invention exhibits a synergistic effect in certain applications (i.e. an effect which is greater than the additive effect of the bacteria when used separately).

In one embodiment, the bacterial strains or a mixture thereof according to the present invention is used in combination with one or more fibres and/or prebiotic.

Suitably, the prebiotic used is polydextrose, lactitol, inositol, L-Arabinose, D-Xylose, L-Rhamnose, D-Mannose, L-Fucose, sorbitol, mannitol, xylitol, fructose, carrageenan, alginate, 5 microcrystalline cellulose (MCC), milk oligosaccharide or betaine.

In a further aspect, the invention relates to a composition, food products, food ingredient, dietary supplements or a pharmaceutical acceptable composition comprising bacterial strains according to the present invention or a mixture thereof and one or more fibres and/or a prebiotic.

EMBODIMENTS OF THE INVENTION

For the avoidance of doubt, some of the embodiments the present invention relates to are set out below:

Embodiment 1. Bacterial strain of the genus *Bifidobacterium* or a mixture thereof for use in preventing or treating illness and/or symptoms associated with coronaviruses in a subject in need thereof.

Embodiment 2. The bacterial strain for use according to embodiment 1, wherein the strain of the genus *Bifidobacterium* is a strain of the species *Bifidobacterium longum* subsp. *Infantis*.

Embodiment 3. The bacterial strain for use according to embodiment 1, wherein the strain of the genus *Bifidobacterium* is a strain of the species *Bifidobacterium animalis* subsp. *lactis*.

Embodiment 4. The bacterial strain for use according to embodiment 2, wherein the strain of the species *Bifidobacterium longum* subsp. *infantis* is strain Bi-26.

Embodiment 5. The bacterial strain for use according to embodiment 3, wherein the strain of the species *Bifidobacterium animalis* subsp. *lactis* is strain Bl-04.

Embodiment 6. The bacterial strain for use according to embodiment 3, wherein the strain of the species *Bifidobacterium animalis* subsp. *lactis* is strain Bi-07.

Embodiment 7. Bacterial strain of the genus *Lacticaseibacillus* or a mixture thereof for use in preventing or treating illness and/or symptoms associated with coronaviruses in a subject in need thereof.

Embodiment 8. The bacterial strain for use according to embodiment 7, wherein the strain of the genus *Lacticaseibacillus* is a strain of the species *Lacticaseibacillus paracasei*.

Embodiment 9. The bacterial strain for use according to embodiment 7, wherein the strain of the genus *Lacticaseibacillus* is a strain of the species *Lacticaseibacillus rhamnosus*.

Embodiment 10. The bacterial strain for use according to embodiment 8, wherein the strain of the species *Lacticaseibacillus paracasei* is strain Lpc-37.

Embodiment 11. The bacterial strain for use according to embodiment 9, wherein the strain of the species *Lacticaseibacillus rhamnosus* is strain Lr-32.

Embodiment 12. The bacterial strain for use according to embodiment 9, wherein the strain of the species *Lacticaseibacillus rhamnosus* is strain GG.

Embodiment 13. Bacterial strain of the genus *Ligilactobacillus* or a mixture thereof for use in preventing or treating illness and/or symptoms associated with coronaviruses in a subject in need thereof.

Embodiment 14. The bacterial strain for use according to embodiment 13, wherein the strain of the genus *Ligilactobacillus* is a strain of the species *Ligilactobacillus salivarius*.

Embodiment 15. The bacterial strain for use according to embodiment 14, wherein the strain of the species *Ligilactobacillus salivarius* is strain Ls-33.

Embodiment 16. Bacterial strain of the genus *Lactobacillus* or a mixture thereof for use in preventing or treating illness and/or symptoms associated with coronaviruses in a subject in need thereof.

Embodiment 17. The bacterial strain for use according to embodiment 16, wherein the strain of the genus *Lactobacillus* is a strain of the species *Lactobacillus acidophilus*.

Embodiment 18. The bacterial strain for use according to embodiment 17, wherein the strain of the species *Lactobacillus acidophilus* is strain NCFM.

Embodiment 19. Bacterial strain of the genus *Limosilactobacillus* or a mixture thereof for use in preventing or treating illness and/or symptoms associated with coronaviruses in a subject in need thereof.

Embodiment 20. The bacterial strain for use according to embodiment 19, wherein the strain of the genus *Limosilactobacillus* is a strain of the species *Limosilactobacillus fermentum*.

Embodiment 21. The bacterial strain for use according to embodiment 20, wherein the strain of the species *Limosilactobacillus fermentum* is strain SBS-1.

Embodiment 22. Bacterial strain of the genus *Lactococcus* or a mixture thereof for use in preventing or treating illness and/or symptoms associated with coronaviruses in a subject in need thereof.

Embodiment 23. The bacterial strain for use according to embodiment 22, wherein the strain of the genus *Lactococcus* is a strain of the species *Lactococcus lactis*.

Embodiment 24. The bacterial strain for use according to embodiment 23, wherein the strain of the species *Lactococcus lactis* is strain Ll-23.

Embodiment 25. Bacterial strain of the genus *Streptococcus* or a mixture thereof for use in preventing or treating illness and/or symptoms associated with coronaviruses in a subject in need thereof.

Embodiment 26. The bacterial strain for use according to embodiment 25, wherein the strain of the genus *Streptococcus* is a strain of the species *Streptococcus thermophilus*.

Embodiment 27. The bacterial strain for use according to embodiment 26, wherein the strain of the species *Streptococcus thermophilus* is strain St-21.

Embodiment 28. The bacterial strain for use according to any one of the preceding embodiments, wherein said illness is a respiratory illness.

Embodiment 29. The bacterial strain for use according to embodiment 28, wherein the respiratory illness is acute respiratory distress syndrome (ARDS).

Embodiment 30. The bacterial strain for use according to embodiment 28, wherein the respiratory illness is pneumonia.

Embodiment 31. The bacterial strain for use according to any one of the embodiments 1-27, wherein said symptoms are one or more of cough, fever, shortness of breath or difficulty breathing (dyspnea), fatigue, muscle or body aches, nausea or vomiting, diarrhea, loss or change of sense of smell (anosmia), and loss or change of sense of taste (ageusia).

Embodiment 32. The bacterial strain for use according to any one of the embodiments 1-27, wherein said preventing or treating is achieved by stimulation of the immune system in the subject when in contact with the bacterial strains as described in any one of embodiments 1-27.

Embodiment 33. The bacterial strain for use according to any one of the embodiments 1-32, wherein the coronavirus is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

Embodiment 34. The bacterial strain for use according to embodiment 33, wherein the coronavirus is SARS-CoV-2 virus.

Embodiment 35. The bacterial strain for use according to any one of embodiments 1-34, wherein the subject has one or more pre-existing conditions selected from the group consisting of obesity, type II diabetes, chronic lung disease or moderate to severe asthma, heart conditions, immunocompromised, chronic kidney disease, liver disease.

Embodiment 36. The bacterial strain for use according to embodiment 34 or embodiment 35, wherein the subject is 65 years of age or older and/or is a resident in a nursing home or long-term care facility or jail or prison.

Embodiment 37. A composition comprising one or more bacterial strains chosen from the genera *Bifidobacterium, Lacticaseibacillus, Ligilactobacillus, Lactobacillus, Limosilactobacillus, Lactococcus* and *Streptococcus*.

Embodiment 38. The composition according to embodiment 37, wherein the strain of the genus *Bifidobacterium* is of the species *Bifidobacterium longum* subsp. *infantis* or *Bifidobacterium animalis* subsp. *lactis*; the strain of the genus *Lacticaseibacillus* is of the species *Lacticaseibacillus paracasei* or *Lacticaseibacillus rhamnosus*; the strain of the genus *Ligilactobacillus* is of the species *Ligilactobacillus salivarius*, the strain of the genus *Lactobacillus* is of the species *Lactobacillus acidophilus*, the strain of the genus *Limosilactobacillus* is of the species *Limosilactobacillus fermentum*; the strain of the genus *Lactococcus* is of the species *Lactococcus lactis* and the strain of the genus *Streptococcus* is of the species *Streptococcus thermophilus*.

Embodiment 39. The composition according to embodiment 38, wherein the *Bifidobacterium longum* subsp. *infantis* is strain Bi-26; the *Bifidobacterium animalis* subsp. *lactis* is strain Bl-04; the *Lacticaseibacillus paracasei* is strain Lpc-37; the *Lacticaseibacillus rhamnosus* is strain Lr-32 and/or strain GG and the *Ligilactobacillus salivarius* is strain Ls-33.

Embodiment 40. The composition according to embodiment 38, wherein the *Bifidobacterium animalis* subsp. *lactis* is strain Bi-07; *Lactobacillus acidophilus* is strain NCFM; *Limosilactobacillus fermentum* is strain SBS-1; *Lactococcus lactis* is strain Ll-23 and *Streptococcus thermophilus* is strain St-21.

Embodiment 41. The composition according to any one of embodiments 37-40, for use in preventing or treating illness and/or symptoms associated with coronaviruses in a subject in need thereof.

Embodiment 42. Use of the composition as described in any one of embodiments 37-40 for preventing or treating illness and/or symptoms associated with coronaviruses in a subject in need thereof.

Embodiment 43. The composition for use according to embodiment 41, wherein the coronavirus is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

Embodiment 44. The use according to embodiment 42, wherein the coronavirus is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

Embodiment 45. The composition for use according to embodiment 41, wherein the coronavirus is SARS-CoV-2 virus.

Embodiment 46. The use according to embodiment 42, wherein the coronavirus is SARS-CoV-2 virus.

Embodiment 47. The composition according to embodiment 41 or embodiment 42, wherein the subject has one or more pre-existing conditions selected from the group consisting of obesity, type II diabetes, chronic lung disease or moderate to severe asthma, heart conditions, immunocompromised, chronic kidney disease and liver disease.

Embodiment 48. The composition according to embodiment 41 or embodiment 42, wherein the subject is 65 years of age or older and/or is a resident in a nursing home or long-term care facility or jail or prison.

Embodiment 49. The composition according to embodiment 41 or 42, wherein said illness is a respiratory illness.

Embodiment 50. The composition according to embodiment 49, wherein the respiratory illness is acute respiratory distress syndrome (ARDS).

Embodiment 51. The composition according to embodiment 49, wherein the respiratory illness is pneumonia.

Embodiment 52. The composition according to embodiment 41 or 42, wherein said symptoms are one or more of shortness of breath or difficulty breathing (dyspnea), fatigue, muscle or body aches, nausea or vomiting, diarrhea, cough, fever, loss or change of sense of smell (anosmia) and loss or change of sense of taste (ageusia).

Embodiment 53. The composition according to embodiment 41 or 42, wherein said preventing or treating is achieved by stimulation of the immune system in the subject when in contact with the composition as described in embodiments 37-40.

Embodiment 54. The composition according to any one of embodiments 37-53, wherein said composition is a food product, food ingredient, a dietary supplement or a pharmaceutical acceptable composition.

Embodiment 55. A method of treating or preventing illness and/or symptoms associated with coronaviruses in a subject in need thereof, said method comprising administering a bacterial strain of the genus *Bifidobacterium* or a mixture thereof to said subject.

Embodiment 56. The method according to embodiment 55, wherein the strain of the genus *Bifidobacterium* is a strain of the species *Bifidobacterium longum* subsp. *Infantis*.

Embodiment 57. The method according to embodiment 55, wherein the strain of the genus *Bifidobacterium* is a strain of the species *Bifidobacterium* animalis subsp. *lactis*.

Embodiment 58. The method according to embodiment 56, wherein the strain of the species *Bifidobacterium longum* subsp. *infantis* is strain Bi-26.

Embodiment 59. The method according to embodiment 57, wherein the strain of the species *Bifidobacterium* animalis subsp. *lactis* is strain Bl-04.

Embodiment 60. The method according to embodiment 57, wherein the strain of the species *Bifidobacterium* animalis subsp. *lactis* is strain Bi-07.

Embodiment 61. A method of treating or preventing illness and/or symptoms associated with coronaviruses in a subject in need thereof, said method comprising administering a bacterial strain of the genus *Lacticaseibacillus* or a mixture thereof to said subject.

Embodiment 62. The method according to embodiment 61, wherein the strain of the genus *Lacticaseibacillus* is a strain of the species *Lacticaseibacillus paracasei*.

Embodiment 63. The method according to embodiment 61, wherein the strain of the genus *Lacticaseibacillus* is a strain of the species *Lacticaseibacillus rhamnosus*.

Embodiment 64. The method according to embodiment 62, wherein the strain of the species *Lacticaseibacillus paracasei* is strain Lpc-37.

Embodiment 65. The method according to embodiment 63, wherein the strain of the species *Lacticaseibacillus rhamnosus* is strain Lr-32.

Embodiment 66. The method according to embodiment 63, wherein the strain of the species *Lacticaseibacillus rhamnosus* is strain GG.

Embodiment 67. A method of treating or preventing illness and/or symptoms associated with coronaviruses in a subject in need thereof, said method comprising administering a bacterial strain of the genus *Ligilactobacillus* or a mixture thereof to said subject.

Embodiment 68. The method according to embodiment 67, wherein the strain of the genus *Ligilactobacillus* is a strain of the species *Ligilactobacillus* salivarius.

Embodiment 69. The method according to embodiment 68, wherein the strain of the species *Ligilactobacillus salivarius* is strain Ls-33.

Embodiment 70. A method of treating or preventing illness and/or symptoms associated with coronaviruses in a subject in need thereof, said method comprising administering a bacterial strain of the genus *Lactobacillus* or a mixture thereof to said subject.

Embodiment 71. The method according to embodiment 70, wherein the strain of the genus *Lactobacillus* is a strain of the species *Lactobacillus acidophilus*.

Embodiment 72. The method according to embodiment 71, wherein the strain of the species *Lactobacillus acidophilus* is strain NCFM.

Embodiment 73. A method of treating or preventing illness and/or symptoms associated with coronaviruses in a subject in need thereof, said method comprising administering a bacterial strain of the genus *Limosilactobacillus* or a mixture thereof to said subject.

Embodiment 74. The method according to embodiment 73, wherein the strain of the genus *Limosilactobacillus* is a strain of the species *Limosilactobacillus* fermentum.

Embodiment 75. The method according to embodiment 74, wherein the strain of the species *Limosilactobacillus fermentum* is strain SBS-1.

Embodiment 76. A method of treating or preventing illness and/or symptoms associated with coronaviruses in a subject in need thereof, said method comprising administering a bacterial strain of the genus *Lactococcus* or a mixture thereof to said subject.

Embodiment 77. The method according to embodiment 76, wherein the strain of the genus *Lactococcus* is a strain of the species *Lactococcus lactis*.

Embodiment 78. The method according to embodiment 77, wherein the strain of the species *Lactococcus lactis* is strain Ll-23.

Embodiment 79. A method of treating or preventing illness and/or symptoms associated with coronaviruses in a subject in need thereof, said method comprising administering a bacterial strain of the genus *Streptococcus* or a mixture thereof to said subject.

Embodiment 80. The method according to embodiment 79, wherein the strain of the genus *Streptococcus* is a strain of the species *Streptococcus thermophilus*.

Embodiment 81. The method according to embodiment 80, wherein the strain of the species *Streptococcus* thermophilus is strain St-21.

Embodiment 82. The method according to any one of the embodiments 55-81, wherein said illness is a respiratory illness.

Embodiment 83. The method according to embodiment 82, wherein the respiratory illness is acute respiratory distress syndrome (ARDS).

Embodiment 84. The method according to embodiment 82, wherein the respiratory illness is pneumonia.

Embodiment 85. The method according to any one of the embodiments 55-81, wherein said symptoms are one or more of shortness of breath or difficulty breathing (dyspnea), fatigue, muscle or body aches, nausea or vomiting, diarrhea, cough, fever, loss or change of sense of smell (anosmia) and loss or change of sense of taste (ageusia).

Embodiment 86. The method according to any one of the embodiments 55-85, wherein said preventing or treating is achieved by stimulation of the immune system in the subject when in contact with the bacterial strains as described in embodiments 55-81.

Embodiment 87. The method according to any one of embodiments 55-86, wherein the coronavirus is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

Embodiment 88. The method according to embodiment 87, wherein the coronavirus is SARS-CoV-2 virus.

Embodiment 89. The method according to any one of embodiments 55-88, wherein the subject has one or more pre-existing conditions selected from the group consisting of obesity, type II diabetes, chronic lung disease or moderate to severe asthma, heart conditions, immunocompromised, chronic kidney disease and liver disease.

Embodiment 90. The method according to any one of embodiments 55-89, wherein the subject is 65 years of age or older and/or is a resident in a nursing home or long-term care facility or jail or prison.

Embodiment 91. Use of a bacterial strain of the genus *Bifidobacterium* or a mixture thereof for preventing or treating illness and/or symptoms associated with coronaviruses in a subject in need thereof.

Embodiment 92. The use according to embodiment 91, wherein the strain of the genus *Bifidobacterium* is a strain of the species *Bifidobacterium longum* subsp. *Infantis*.

Embodiment 93. The use according to embodiment 91, wherein the strain of the genus *Bifidobacterium* is a strain of the species *Bifidobacterium* animalis subsp. *lactis*.

Embodiment 94. The use according to embodiment 92, wherein the strain of the species *Bifidobacterium longum* subsp. *infantis* is strain Bi-26.

Embodiment 95. The use according to embodiment 93, wherein the strain of the species *Bifidobacterium* animalis subsp. *lactis* is strain Bl-04.

Embodiment 96. The use according to embodiment 93, wherein the strain of the species *Bifidobacterium* animalis subsp. *lactis* is strain Bi-07.

Embodiment 97. Use of a bacterial strain of the genus *Lacticaseibacillus* or a mixture thereof for preventing or treating illness and/or symptoms associated with coronaviruses in a subject in need thereof.

Embodiment 98. The use according to embodiment 97, wherein the strain of the genus *Lacticaseibacillus* is a strain of the species *Lacticaseibacillus paracasei*.

Embodiment 99. The use according to embodiment 97, wherein the strain of the genus *Lacticaseibacillus* is a strain of the species *Lacticaseibacillus rhamnosus*.

Embodiment 100. The use according to embodiment 98, wherein the strain of the species *Lacticaseibacillus paracasei* is strain Lpc-37.

Embodiment 101. The use according to embodiment 99, wherein the strain of the species *Lacticaseibacillus rhamnosus* is strain Lr-32.

Embodiment 102. The use according to embodiment 99, wherein the strain of the species *Lacticaseibacillus rhamnosus* is strain GG.

Embodiment 103. Use of a bacterial strain of the genus *Ligilactobacillus* or a mixture thereof for preventing or treating illness and/or symptoms associated with coronaviruses in a subject in need thereof.

Embodiment 104. The use according to embodiment 103, wherein the strain of the genus *Ligilactobacillus* is a strain of the species *Ligilactobacillus* salivarius.

Embodiment 105. The use according to embodiment 104, wherein the strain of the species *Ligilactobacillus salivarius* is strain Ls-33.

Embodiment 106. Use of a bacterial strain of the genus *Lactobacillus* or a mixture thereof for preventing or treating illness and/or symptoms associated with coronaviruses in a subject in need thereof.

Embodiment 107. The use according to embodiment 106, wherein the strain of the genus *Lactobacillus* is a strain of the species *Lactobacillus acidophilus*.

Embodiment 108. The use according to embodiment 107, wherein the strain of the species *Lactobacillus acidophilus* is strain NCFM.

Embodiment 109. Use of a bacterial strain of the genus *Limosilactobacillus* or a mixture thereof for preventing or treating illness and/or symptoms associated with coronaviruses in a subject in need thereof.

Embodiment 110. The use according to embodiment 109, wherein the strain of the genus *Limosilactobacillus* is a strain of the species *Limosilactobacillus* fermentum.

Embodiment 111. The use according to embodiment 110, wherein the strain of the species *Limosilactobacillus fermentum* is strain SBS-1.

Embodiment 112. Use of a bacterial strain of the genus *Lactococcus* or a mixture thereof for preventing or treating illness and/or symptoms associated with coronaviruses in a subject in need thereof.

Embodiment 113. The use according to embodiment 112, wherein the strain of the genus *Lactococcus* is a strain of the species *Lactococcus lactis*.

Embodiment 114. The use according to embodiment 113, wherein the strain of the species *Lactococcus lactis* is strain Ll-23.

Embodiment 115. Use of a bacterial strain of the genus *Streptococcus* or a mixture thereof for preventing or treating illness and/or symptoms associated with coronaviruses in a subject in need thereof.

Embodiment 116. The use according to embodiment 115, wherein the strain of the genus *Streptococcus* is a strain of the species *Streptococcus thermophilus*.

Embodiment 117. The use according to embodiment 116, wherein the strain of the species *Streptococcus* thermophilus is strain St-21.

Embodiment 118. The use according to any one of the embodiments 91-117, wherein said illness is a respiratory illness.

Embodiment 119. The use according to embodiment 118, wherein the respiratory illness is acute respiratory distress syndrome (ARDS).

Embodiment 120. The use according to embodiment 118, wherein the respiratory illness is pneumonia.

Embodiment 121. The use according to any one of the embodiments 91-117, wherein said symptoms are one or more of shortness of breath or difficulty breathing (dyspnea), fatigue, muscle or body aches, nausea or vomiting, diarrhea, cough, fever, loss or change of sense of smell (anosmia) and loss or change of sense of taste (ageusia).

Embodiment 122. The use according to any one of the embodiments 91-117, wherein said preventing or treating is achieved by stimulation of the immune system in the subject when in contact with the bacterial strains as described in embodiments 91-117.

Embodiment 123. The use according to any one of embodiments 91-117, wherein the coronavirus is selected from the group consisting of 229E (alpha coronavirus), NL63 (alpha coronavirus), OC43 (beta coronavirus), HKU1 (beta coronavirus), MERS-CoV (Middle East Respiratory Syndrome coronavirus), SARS-CoV, and SARS-CoV-2 virus.

Embodiment 124. The use according to any one of embodiments 91-117, wherein the coronavirus is SARS-CoV-2 virus.

Embodiment 125. The use according to any one of embodiments 91-124, wherein the subject has one or more pre-existing conditions selected from the group consisting of obesity, type II diabetes, chronic lung disease or moderate to severe asthma, heart conditions, immunocompromised, chronic kidney disease and liver disease.

Embodiment 126. The use according to any one of embodiments 91-125, wherein the subject is 65 years of age or older and/or is a resident in a nursing home or long-term care facility or jail or prison.

EXAMPLES

Experimental

Phase 1: In-Silico and In Vitro Potential of Immunogenicity/Cross-Reactivity: Microbial Cross-Reactive Antigens (mCRAGs)

Pre-Selection of Probiotic Strains: In Silico Screening

Using SARS-CoV-2 predicted epitopes for CD4, CD8, B-cells (Grifoni A, Sidney J, Zhang Y, Scheuermann R H, Peters B, Sette A; *A Sequence Homology and Bioinformatic Approach Can Predict Candidate Targets for Immune Responses to SARS-CoV-2; Cell Host Microbe;* 2020; 27(4): 671-80 e2) we are performing BLAST homology searches against our commercial probiotic genomes to identify potential cross-reactive peptides. Matches are assessed by alignment length, overall homology, number of matches per strain, and location of the match (e.g. extracellular proteins). Probiotic peptides and strains containing the best cross-reactive matches are being selected for further characterization in vitro and in vivo.

Two in vitro validation approaches are being performed that test the probiotic peptides recognition by T-cells and also the whole probiotic cell interactions with SARS-CoV-2 antibodies.

In Vitro Approach 1: Peptide Screening

Peptides libraries (5 per epitope sequence overlapping by 1 amino acid) are synthesized. CD8 epitopes are 9-mers, CD4 epitopes are 15 mers. They are tested for immune response.

Dendritic cells are prepared from peripheral mononuclear blood cells (PBMC) from donor Buffy coat material. The dendritic cells are incubated with the peptides and either autologous CD4 or CD8 Tcells. Those peptides eliciting a T-cell response are identified For peptides that elicit a T-cell response, the same assay is performed with the intact bacterial protein, to confirm that the dendritic cell presents the epitope from the processed protein.

In Vitro Approach 2: Whole Cell Screening.

Biolayer interferometry (BLI) using the Octet HTX system (Molecular Devices) is used to detect bacterial proteins that cross react with specificity to anti-SARS-CoV-2 antibodies. Both direct and indirect modes of detection are used to screen lysates for binding activity. Octet based methods utilize High Precision Streptavidin (SAX) Biosensors, (ForteBio). Bacterial lysates are made using BugBuster Reagent (Novagen) supplemented with mutanolysin (Sigma), lysozyme (Thermo), Benzonase (Novagen), and Halt protease inhibitor cocktail (Pierce).

Direct binding assays: Affinity purified polyclonal antibodies raised in rabbits against various SARS-CoV-2 antigens including the RBD, S1, and full S1-S2 ectodomains (Sino Biological) are labeled with biotin (Chromalink, Tri-Link Biotechnologies). Control probes are created using off target and irrelevant rabbit polyclonal antibodies. Biotinylated antibodies are loaded onto streptavidin probes then free biotin binding pockets are quenched using a solution containing Biocytin (Tocris). Antibody functionalized probes are used to interrogate lysate samples for binding activity. Positive BLI association signal relative to control biosensors are considered indicative of cross-reactive epitope containing proteins in the solution.

Indirect binding assays: For indirect assays the streptavidin probes are functionalized using a recombinant biotin labeled SARS-CoV-2 S1 antigen (Sino Biological). Solutions containing polyclonal or monoclonal antibodies are incubated together with microbial lysates and binding to the antigen functionalized probes are measured. Lysates able to reduce binding of antibodies to the antigen probe are considered positive for cross-reactive bacterial proteins.

Western Blots: Bacterial lysates are electrophoretically separated by sodium dodecyl sulfate-polyacrylamide gel electrophoresis (SDS-PAGE). Separated proteins are transferred onto nitrocellulose membranes using a semi-dry transfer system (Power Blotter, Thermo Fisher). Blots are blocked using Odyssey PBS based blocking buffer for at least 1 hour followed by incubation with anti-SARS-CoV-2 antibodies. Horse Radish Peroxidae (HRP) conjugated anti-rabbit or anti-human IgG is used to detect anti-SARS-CoV-2 bound to microbial proteins. Enzyme coupled signal to detect antibody bound proteins used Chromagenic HRP (TMB) detection solution (Novex). Blots are washed between incubations and enzyme coupled detection steps with Phosphate Buffered Saline (PBS) containing 0.1% Bovine Serum Albumin (BSA).

Flow Cytometry: To detect cross reactive surface antigens we use whole cell bacteria grown under various optimal growth conditions. Bacterial cells are collected at time intervals and washed by 3 cycles of centrifugation and resuspension in PBS 0.1% BSA. Washed cells are incubated at room temperature in PBSA with anti-SARS-CoV-2 antibodies after which the cells are washed by 3 cycles of centrifugation and resuspension in PBSA. Antibody labeled cells are incubated with anti-rabbit or human IgG alexaFluor-488 (Invitrogen) and Syto 62 (Invitrogen). After 30 minutes with secondary antibodies the fluorescent intensity of the cells is measured on a Quanteon Flow Cytometer (ACEA BioSciences). Triggering thresholds are set to meet a minimal signal strength determined by the Syto 62 fluorescent intensity determined empirically by cell type to exclude non cellular events. At least 20,000 events are collected for each sample and compared to cells incubated with control antibodies. Cells with significantly higher AlexaFluor-488 signal compared to control antibodies are considered to express surface antigens cross-reactive with SARS-CoV-2 antigens.

Phase 1b: Dendritic Cell Stimulation by Probiotics

The probiotic bacteria will be tested in a human blood derived dendritic cell model.

Bacteria

Probiotic strains (DGCC, Danisco Global Culture collection, Niebüll, Germany) are grown to logarithmic growth phase, collected by centrifugation, washed once with PBS and suspended to cell culture medium. The OD600 will be adjusted to correspond to bacteria:host cell ratio of 10:1.

Monocyte Purification and Differentiation to Macrophages and Dendritic Cells

Monocytes are purified from freshly collected leukocyte-rich buffy coats obtained from healthy blood donors. Human peripheral blood mononuclear cells are isolated by density gradient centrifugation followed by purification of monocytes with CD14+ magnetic beads. To obtain macrophages purified monocytes are plated on 24 well plates $3 \times 10^5$ cells/well and cultured 7 d in Macrophage-SFM (Gibco, Life Technologies, Grand Island, NY, USA) with recombinant human GM-CSF (Miltenyi Biotech) 1000 IU/ml and 1% Antibiotic-Antimycotic. To differentiate monocytes into immature dendritic cells, monocytes are plated on 12 well plates $5 \times 10^5$ cells/well (Falcon, Corning, NY, USA) and cultured for 7 d in RPMI-1640 (Sigma) supplemented with 1% Antibiotic-Antimycotic, 10% fetal bovine serum (FBS), IL-4 (400 IU/ml) and GM-CSF (1000 IU/ml).

Stimulation of Immune Cells

Cells from six blood donors are stimulated with probiotic bacteria alone (bacteria:cell ratio of 10:1) or in combination with TLR ligand blend, Poly I:C, 30 µg/ml+R848, 10 µM (both from Sigma-Aldrich, St. Louis, MO, USA) for 24 h.

ELISA Analysis

Cell culture supernatants from macrophage and dendritic cell cultures are analyzed for IFN-γ, IL-1β, IL-6, IL-10, IL-12p70, and TNF-α by Aushon Human 6-Plex Ciraplex Array (Aushon BioSystems, Inc., Billerica, MA, USA). In addition, dendritic cell supernatants are analyzed for IL-23 and TGF-β by Aushon Human 1-plex Assays according to manufacturer's instructions. Results will be analyzed with CiraSoft software (Aushon Biosystems).

Phase 1c: The Effect of *B. lactis* Bl-04 on Coronavirus Receptor Expression in a Mouse Model of Influenza Infection Probiotic Bl-04 or vehicle is administered at $2*10^9$ CFU/day to BALB/c mice over 21 days before giving nasal influenza A virus (California/07/2009) infection to mice at study day 0 (D0). The mice are monitored D14 post-infection. Tissue samples for transcriptomics are taken from small intestine, blood, and lungs at days D-21, D-20, D-18, D-14, D-7, D0, D3, D5, D7, D14. Viral load will be analysed D3, D5, and D7, and health scores assessed D0-D14.

Transcriptomics Analysis of Coronavirus Receptors

RNA is extracted from the tissue samples and sequenced. The regulation of coronavirus related receptor expression, ACE2, and its potential regulators, including but not limited to ADAM17, Furin, TMPRSS2, and AGTR1 are analyzed.

Figure 18:
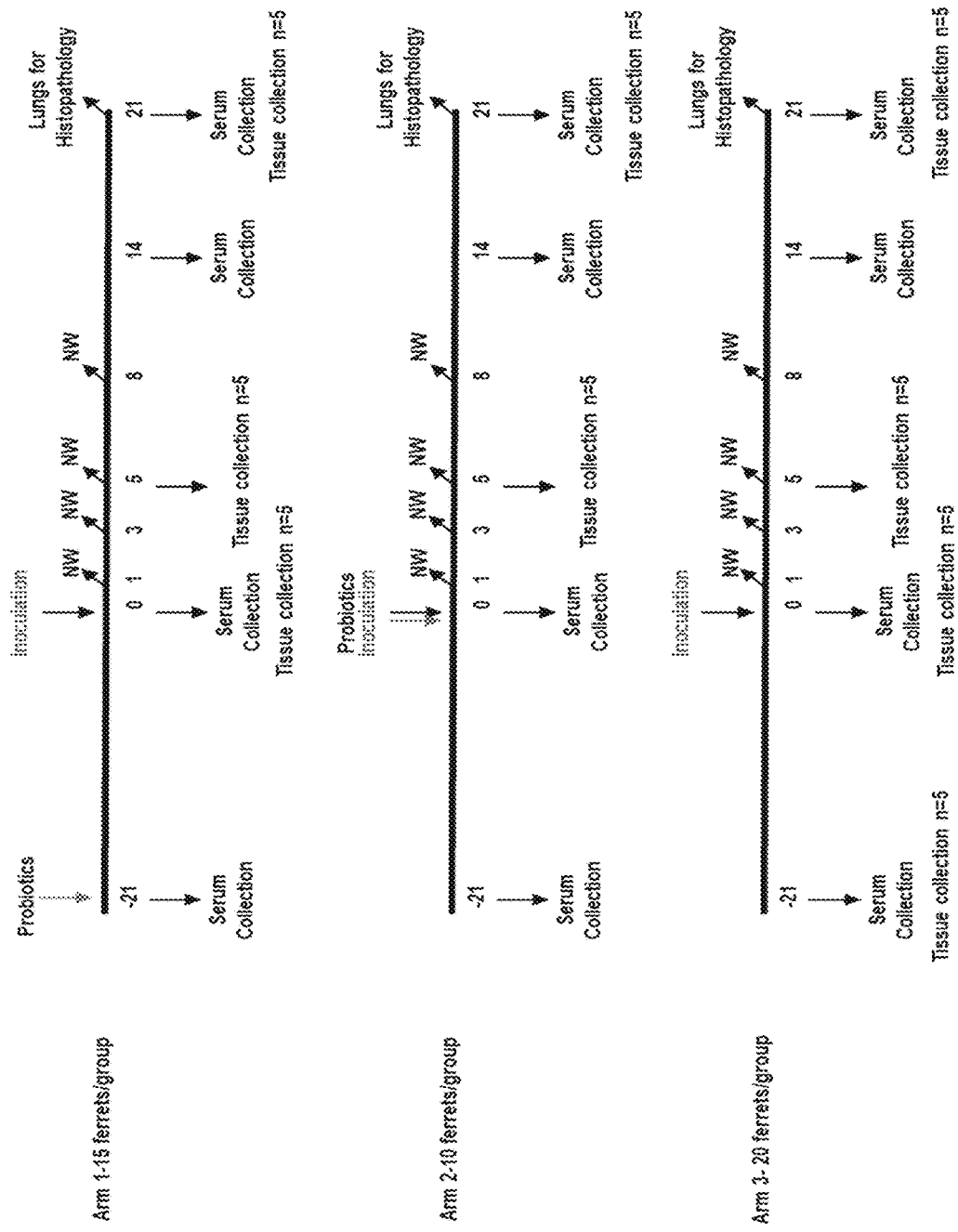
FIG. 18 depicts a diagram of the experimental design used in Example 1.

Phase 2: Microbial Cross-Reactive Antigens (mCRAGs)—Proof of Concept Pre-Clinical Experimental Design Ferrets are gavaged with probiotic strains consortia before (Arm 1) and after (Arm 2) the inoculation with virus as shown in the design in FIG. 18.

Endpoints:
  i. Nasal wash titers,
  ii. Lung histopathology,
  iii. GI histopathology
  iv. Cytokine expression,
  v. Antibody profiling,
  vi. Metagenomics.

Phase 3: Proof of Concept Clinical

To test the efficacy of the probiotic bacterial strains to improve antibody and T-cell responses and to stimulate innate immunity in healthy humans.

Subjects (n): 20-40 subjects

Product: bacterial strains chosen from strains Bi-26, Bl-04, Bi-07, Lpc-37, Lr-32, GG, Ls-33, NCFM, SBS-1, Ll-23 and St-21 or compositions comprising one or more of these bacterial strains.

Dose: range $10^6$-$10^{12}$; $10^8$-$10^{12}$, $10^9$-$10^{11}$

Inclusion criteria: healthy adults 18-35 years of age.

Human Leucocyte Antigen (HLA) typing—to check if dependent on HLA type/need to screen for certain HLA types.

Design: Open label, single arm, pre-post supplementation.

Supplementation period: 4 weeks.

Primary outcome: Increase in specific respiratory tract mucosal IgA against SARS-CoV-2 (Spike protein).

Secondary outcomes: (i) Fecal secretory IgA total/specific (S/SARS-CoV-2/bacterial strain or consortia), Neutralizing Ab test; (i) Saliva/Nasal (or bronchoalveolar) lavage IgA total/specific (S/SARS-CoV-2/bacterial strain or consortia), Neutralizing Ab test; (iii) Serum Ab IgG/A/M totals and specific (S/SARS-CoV-2/bacterial strain or consortia), Neutralizing Ab test; (iv) Blood T-cell response (peptide/peptide pool PBMC incubation and ELISPOT; flow cytometry and T-cell phenotyping); Also, option to use pMHCII tetramers to check for the epitope specific T-cells. Transcriptomes of the nasal epithelium to test for (innate) immune system changes.

Phase 4: Human Clinical Efficacy Trial

The effect of probiotic strains Bi-26, Bl-04, Lpc-37, Lr-32, Ls-33, GG, Bi-07, NCFM, SBS-1, Ll-23 and St-21 or compositions comprising one or more of these bacterial strains on reducing the risk of SARS-CoV-2 infection and reducing the severity of COVID-19 disease course.

Randomized double-blind placebo controlled clinical trial.

Subjects (n): 300-400 negative for SARS-CoV-2 and in increased risk of infection (e.g. health care workers).

Supplementation time: 5 months.

Primary Outcome: Risk of SARS-CoV-2 infection.

Secondary Outcomes: Risk, duration and severity of COVID-19.

Exploratory Outcomes: Neutralizing antibodies, T-cell responses, mucosal and systemic (innate) immune function.

Example 1: Isolation and Identification of Cross-Reactive Proteins Expressed by Probiotic Bacteria Strains Preparation of bacterial lysates: Bacterial strains were streaked out on MRS Agar plates and grown under anaerobic conditions at 37° C. overnight. Single colonies were picked and transferred to 2.0 mls of MRS broth and grown for 4-8 hrs then transferred to 100 ml flasks with 30 mls MRS and incubated at 37° C. for approximately 40 hours in an anaerobic chamber with atmospheric conditions set to the following levels; 85% nitrogen, 10% carbon dioxide, and 5% hydrogen. Stationary growth cultures were harvested, and cells were pelleted by centrifugation at 8000×g for 5 minutes. Cells were washed twice with PBS then the wet weight of the pellet was measured. Whole cell lysates were then prepared by resuspending the pellet at 100 mg wet cell mass per ml of extraction buffer [50 mM tris-HCl pH 8.0, 30% [w/v] sucrose, 5 mM $MgCl_2$, 5 mM $CaCl_2$), 4 mg/mL lysozyme, and 150 U/mL mutanolysin, Halt protease inhibitor cocktail] and incubated for 3 hours at 37° C. Extraction buffer treated cells were disrupted using 0.1 um zirconia-silica bead and beating for 3 minutes at max speed in a bead beater (Bullet Blender Gold, Next Advance). Insoluble material was removed by centrifugation at 16K×g for 5 minutes and supernatant were stored frozen at −80° C.

Immunoprecipitation: Affinity purified rabbit polyclonal antibodies raised against recombinant SARS-CoV-2 spike antigen covering the entire extracellular domain were obtained from Sino Biological Catalog #40589-T62. Antibodies were labeled with biotin using a commercial labeling kit (ChromaLINK® Biotin Protein Labeling Kit (TriLink B-(007-105). Biotin labeled antibodies were incubated with Dynabeads™ MyOne™ Streptavidin C1 (Invitrogen #65001) according to manufacturer recommendations. The magnetic beads functionalized with antibodies were incubated with whole cell lysates produced from probiotic strains as described in the methods section for Octet binding assays. The beads were incubated with the lysates overnight at 4° C. after which the beads were pulled from the lysate with a strong magnet followed by three washed in PBS. The probiotic proteins bound to the beads were eluted with a single volume of 100 mM Glycine pH 2.0. The beads were then placed onto a magnet and the elution fraction was transferred to a tube containing 300 µl of 1M Tris pH 8.0 to neutralize the low pH Glycine buffer. The neutralized elution fraction was then filtered using an Amicon microfiltration device with a 3.0 KD MWCO membrane replacing the buffer volume once with 0.2M Tris pH 7.0, 150 mM NaCl and repeating the concentration step to yield a final volume of ~100 ul. The eluted proteins were visualized by separating a portion of the sample on an 4-12% gradient SDS-PAGE gel then silver staining using a commercial kit SilverQuest™ Silver Staining Kit (Invitrogen # LC6070). The remainder of the immunoprecipitated proteins were used for LC/MS analysis to identify the candidate cross reactive epitope containing proteins.

Identification of proteins expressed by probiotic strains that cross react with SARS-CoV-2 antibodies was performed using immunoprecipitation techniques using rabbit SARS-CoV-2 polyclonal antibodies. These experiments yielded pools of proteins visible on silver stained SDS-PAGE gels with similar migration patterns of cross-reactive proteins seen in western blot experiments using the same lysates. Analysis of proteins precipitated using anti-SARS-CoV-2 antibodies by LC/MS analysis of trypsin digests yielded high confidence protein identities which are described in Table 1 and Table 2.

TABLE 1

*Lactobacillus fermentum* SBS-1

| PATRIC Accession # | Function from RAST | Coverage | # Unique Peptides | # AAs | MW [kDa] | Area: F8: Sample |
|---|---|---|---|---|---|---|
| fig\|1613.356.peg.1153 | DNA-binding protein HBsu | 90.1 | 16 | 91 | 9.5 | 8.22E+09 |
| fig\|1613.356.peg.1217 | ABC transporter, substrate-binding (cluster 3, basic aa/glutamine/opines) | 76.4 | 35 | 284 | 31.6 | 2.09E+09 |
| fig\|1613.356.peg.358 | 3-hydroxyacyl-[acyl-carrier-protein] dehydratase, FabZ form (EC 4.2.1.59) | 74.3 | 14 | 144 | 15.7 | 3.22E+08 |
| fig\|1613.356.peg.288 | beta-galactosidase small subunit (EC 3.2.1.23) | 35.3 | 10 | 320 | 35.7 | 2.36E+08 |
| fig\|1613.356.peg.287 | beta-galactosidase large subunit (EC 3.2.1.23) | 15.5 | 6 | 626 | 72.2 | 8.86E+07 |
| fig\|1613.356.peg.743 | ABC transporter, substrate-binding YckB (cluster 3, basic aa/glutamine/opines) | 18.8 | 8 | 287 | 31.7 | 5.08E+07 |
| fig\|1613.356.peg.350 | 3-hydroxyacyl-[acyl-carrier-protein] dehydratase, FabZ form (EC 4.2.1.59) | 31.0 | 6 | 145 | 16.3 | 1.93E+08 |
| fig\|1613.356.peg.2212 | Ribonuclease P protein component (EC 3.1.26.5) | 27.2 | 2 | 114 | 13.3 | 2.47E+07 |
| fig\|1613.356.peg.893 | ABC transporter, ATP-binding protein (cluster 8, B12/iron complex) | 14.8 | 1 | 256 | 28.2 | 3.16E+09 |
| fig\|1613.356.peg.1542 | Ribosome small subunit biogenesis RbfA-release protein RsgA | 13.5 | 1 | 296 | 33.2 | 5.09E+09 |

TABLE 1-continued

*Lactobacillus fermentum* SBS-1

| PATRIC Accession # | Function from RAST | Coverage | # Unique Peptides | # AAs | MW [kDa] | Area: F8: Sample |
|---|---|---|---|---|---|---|
| fig\|1613.356.peg.1917 | hypothetical protein | 12.5 | 4 | 289 | 33.8 | 2.80E+07 |
| fig\|1613.356.peg.1235 | hypothetical protein | 19.0 | 3 | 105 | 13.0 | 3.14E+07 |
| fig\|1613.356.peg.671 | Translation elongation factor Tu | 7.6 | 2 | 396 | 43.4 | 9.43E+06 |
| fig\|1613.356.peg.1136 | DNA topoisomerase I (EC 5.99.1.2) | 2.8 | 2 | 708 | 80.2 | 1.45E+07 |
| fig\|1613.356.peg.443 | Phosphoglucosamine mutase (EC 5.4.2.10) | 1.8 | 1 | 452 | 48.8 | 1.49E+07 |
| fig\|1613.356.peg.432 | 3'-to-5' exoribonuclease RNase R | 2.0 | 1 | 797 | 90.8 | 2.80E+07 |
| fig\|1613.356.peg.124 | Mobile element protein | 8.6 | 1 | 151 | 17.7 | 8.16E+07 |
| fig\|1613.356.peg.1915 | hypothetical protein | 2.2 | 1 | 458 | 52.0 | 5.65E+07 |
| fig\|1613.356.peg.37 | ClpE-like protein | 1.9 | 1 | 697 | 76.6 | 8.01E+06 |
| fig\|1613.356.peg.891 | NADH dehydrogenase (EC 1.6.99.3) | 5.2 | 2 | 407 | 44.0 | 6.61E+06 |
| fig\|1613.356.peg.1071 | ABC transporter, substrate-binding protein (cluster 13, osmolytes) | 3.7 | 1 | 300 | 32.9 | 1.81E+07 |
| fig\|1613.356.peg.337 | Exopolyphosphatase (EC 3.6.1.11) | 6.3 | 2 | 317 | 35.6 | 3.68E+07 |
| fig\|1613.356.peg.202 | Exopolyphosphatase (EC 3.6.1.11) | 8.3 | 2 | 312 | 35.4 | 1.08E+07 |
| fig\|1613.356.peg.1486 | hypothetical protein | 9.8 | 2 | 163 | 19.1 | 1.40E+07 |
| fig\|1613.356.peg.1908 | ISSth1, transposase (orf1), IS3 family | 3.0 | 1 | 232 | 27.9 | 7.65E+06 |
| fig\|1613.356.peg.357 | Biotin carboxyl carrier protein of acetyl-CoA carboxylase | 5.4 | 1 | 148 | 15.9 | 1.12E+07 |
| fig\|1613.356.peg.603 | Hypothetical DUF1027 domain protein | 4.5 | 1 | 178 | 21.0 | 1.52E+07 |
| fig\|1613.356.peg.779 | Dihydrolipoamide acetyltransferase (EC 2.3.1.12) | 3.3 | 1 | 429 | 45.5 | 4.54E+06 |
| fig\|1613.356.peg.886 | ABC transporter, substrate-binding protein (cluster 8, B12/iron complex) | 2.5 | 1 | 354 | 38.5 | 6.68E+06 |
| fig\|1613.356.peg.955 | ISSth1, transposase (orf1), IS3 family | 4.8 | 1 | 208 | 24.9 | 1.69E+06 |
| fig\|1613.356.peg.1137 | Rossmann fold nucleotide-binding protein Smf | 7.9 | 1 | 291 | 32.0 | 1.91E+07 |
| fig\|1613.356.peg.1300 | hypothetical protein | 14.9 | 1 | 121 | 14.1 | 1.66E+07 |
| fig\|1613.356.peg.1343 | Uridine monophosphate kinase (EC 2.7.4.22) | 9.1 | 1 | 241 | 26.0 | 8.83E+06 |
| fig\|1613.356.peg.1921 | D-alanyl-D-alanine carboxypeptidase (EC 3.4.16.4) | 4.1 | 1 | 417 | 45.5 | 2.14E+07 |

TABLE 2

*Lactobacillus rhamnosus* GG

| PATRIC Accession # | Function from RAST | Coverage | # Unique Peptides | # AAs | MW [kDa] | Area: F6: Sample |
|---|---|---|---|---|---|---|
| fig\|568703.30.peg.1654 | ABC transporter, substrate-binding protein OppA (TC 3.A.1.5.1) | 55.28 | 38 | 597 | 66.4 | 9.41E+08 |
| fig\|568703.30.peg.1386 | protein HBsu | 85.71 | 12 | 91 | 9.5 | 1.19E+09 |
| fig\|568703.30.peg.1787 | protein PrsA precursor (EC 5.2.1.8) | 42.33 | 12 | 300 | 33.5 | 2.56E+08 |
| fig\|568703.30.peg.617 | hemagglutinin protein | 13.76 | 7 | 734 | 80.7 | 7.57E+07 |
| fig\|568703.30.peg.2074 | ABC transporter, substrate-binding protein OppA (TC 3.A.1.5.1) | 18.55 | 6 | 539 | 59.4 | 9.09E+07 |
| fig\|568703.30.peg.1188 | ABC transporter substrate-binding protein | 25.36 | 5 | 276 | 30.7 | 3.29E+07 |

TABLE 2-continued

Lactobacillus rhamnosus GG

| PATRIC Accession # | Function from RAST | Coverage | # Unique Peptides | # AAs | MW [kDa] | Area: F6: Sample |
|---|---|---|---|---|---|---|
| fig\|568703.30.peg.2122 | dehydratase, FabZ form (EC 4.2.1.59) | 10.96 | 3 | 146 | 15.9 | 6.11E+07 |
| fig\|568703.30.peg.1625 | kinase (EC 2.7.4.22) | 6.69 | 2 | 239 | 25.9 | 2.83E+07 |
| fig\|568703.30.peg.2856 | PTS system, mannose-specific IIB component (EC 2.7.1.191) | 12.00 | 3 | 325 | 35.4 | 3.76E+07 |
| fig\|568703.30.peg.2536 | domain protein | 19.00 | 2 | 221 | 24.9 | 5.14E+07 |
| fig\|568703.30.peg.2251 | shock protein 60 kDa family chaperone GroEL | 6.07 | 2 | 544 | 57.4 | 3.41E+07 |
| fig\|568703.30.peg.925 | Enolase (EC 4.2.1.11) | 3.23 | 1 | 434 | 47.1 | 3.29E+07 |
| fig\|568703.30.peg.206 | ABC transporter, substrate-binding protein OppA (TC 3.A.1.5.1) | 4.26 | 2 | 540 | 59.8 | 9.38E+06 |
| fig\|568703.30.peg.2868 | ABC transporter, substrate-binding protein UgpB | 2.35 | 1 | 425 | 46.6 | 1.71E+07 |
| fig\|568703.30.peg.922 | glyceraldehyde-3-phosphate dehydrogenase (EC 1.2.1.12) | 2.65 | 1 | 340 | 36.7 | 6.48E+06 |
| fig\|568703.30.peg.7 | gyrase subunit A (EC 5.99.1.3) | 1.26 | 1 | 870 | 96.5 | 7.18E+06 |
| fig\|568703.30.peg.257 | carboxypeptidase (EC 3.4.16.4) | 2.75 | 1 | 436 | 47.0 | 1.67E+07 |
| fig\|568703.30.peg.636 | nuclease (Competence-specific nuclease) (EC 3.1.30.-) | 16.48 | 1 | 273 | 30.4 | 1.72E+08 |
| fig\|568703.30.peg.912 | ABC subunit A | 1.87 | 1 | 964 | 106.1 | 1.52E+07 |
| fig\|568703.30.peg.934 | protein SmpB | 5.73 | 1 | 157 | 18.3 | 9.42E+06 |
| fig\|568703.30.peg.942 | ABC transporter, substrate-binding protein UgpB | 3.66 | 1 | 437 | 48.3 | 9.54E+06 |
| fig\|568703.30.peg.1171 | synthase alpha chain (EC 3.6.3.14) | 5.70 | 2 | 509 | 55.2 | 1.41E+07 |
| fig\|568703.30.peg.1337 | elongation factor Tu | 4.04 | 1 | 396 | 43.5 | 6.90E+06 |
| fig\|568703.30.peg.1361 | protein ClpB (ATP-dependent unfoldase) | 5.53 | 1 | 868 | 96.3 | 1.18E+08 |
| fig\|568703.30.peg.1461 | ligase (EC 6.3.4.3) | 1.80 | 1 | 557 | 58.9 | 3.08E+07 |
| fig\|568703.30.peg.2307 | lipoprotein component of predicted cobalamin ECF transporter | 25.38 | 2 | 130 | 14.2 | 1.99E+07 |
| fig\|568703.30.peg.2420 | protein | 17.41 | 1 | 247 | 27.5 | 1.14E+09 |
| fig\|568703.30.peg.2531 | dehydrogenase (EC 1.1.1.27) | 4.60 | 1 | 326 | 35.5 | 1.80E+07 |
| fig\|568703.30.peg.2862 | peptidoglycan binding domain protein | 8.32 | 1 | 565 | 60.2 | 1.41E+09 |

Example 2: In Vivo Use of Microbial Consortia to Decrease Viral Titer in Mammals This example determined the benefits of two microbial consortia on viral titer in ferrets infected with SARS-CoV-2. Consortium 1 included *Bifidobacterium longum* subsp. *infantis* Bi-26, *Bifidobacterium animalis* subsp. *lactis* Bl-04, *Lacticaseibacillus paracasei* Lpc-37, *Lacticaseibacillus rhamnosus* Lr-32, and *Ligilactobacillus salivarius* Ls-33. Consortium 2 included *Bifidobacterium animalis* subsp. *lactis* Bi-07, *Lactobacillus acidophilus* NCFM, *Limosilactobacillus fermentum* SBS-1, *Lactococcus lactis* Ll-23, and *Streptococcus* thermophilus St-21.

Determination of Viral titers in nasal wash: From day 1 through day 17, ferrets received a daily oral gavage of consortia 1 or consortia 2 or Placebo. On day 8 ferrets were anesthetized with Ketamine/Xylazine and inoculated with $10^5$ PFU 2019 Novel Coronavirus, Isolate USA-WA1/2020 (SARS-CoV-2). On study days 9, 11, 13, 15, 17, and 18, nasal washes were collected and viral load was determined of by RT-qPCR and reported as number of genomes/µl of nasal wash.

RT-qPCR Virus Titers: The concentration of virus in nasal washes from study days 9 (i.e. day one post-infection), 11, 13, 15, 17, and 18 were determined by RT-qPCR assay. Briefly, RNA was extracted from samples stored in RNA/DNA Shield using the Quick-RNA Viral Kit (Zymo Research) according to manufacturer's protocol. RT-qPCR was be performed using the iTaq universal probes one-step kit (Bio-Rad). The following RT-PCR cycling conditions used: 50° C. for 15 min (RT), then 95° C. for 2 min (denature), then 40 cycles of 10 s at 95° C., 45 s at 62° C.

```
Primers used for SARS-CoV-2 detection:
2019-nCoV_N1-F
5'-GACCCCAAAATCAGCGAAAT-3'

2019-nCoV_N1-R
5'-TCTGGTTACTGCCAGTTGAATCTG-3'

Probe: 2019-nCoV_N1-P:
5'-FAM-ACCCCGCATTACGTTTGGTGGACC-BHQ1-3'
```

Figure 1B:
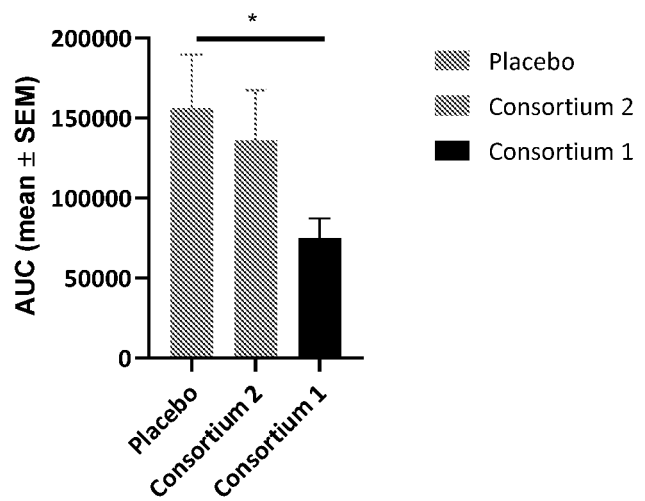
FIG. 1B is a chart showing the area under the curve (AUC) for the treatment and prevention arms of the study as well as the placebo group.

As shown in FIG. 1A and FIG. 1B, animals in the prevention arm exhibited significantly decreased viral titers following infection with SARS-CoV-2 as compared to placebo.

These results show that administration of consortium 1 significantly reduces viral load in a ferret model of COVID-19.

Figure 19:
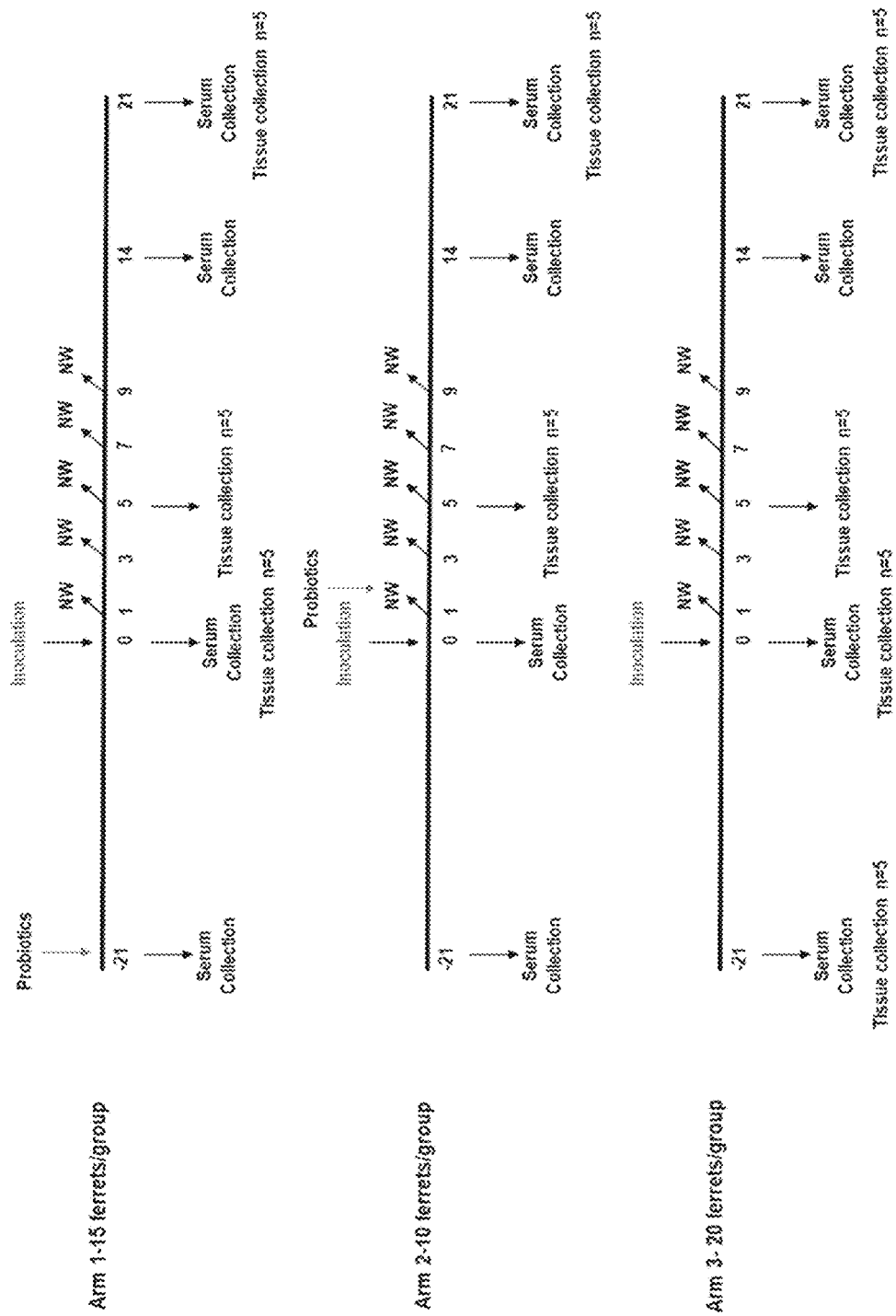
FIG. 19 depicts a diagram of the experimental design used in Example 3.

Example 3: In Vivo Use of Microbial Consortia to Decrease Viral Titer in Mammals This Example replicated the ferret trial described in Example 2 with slight modification of the procedure. Ferrets are gavaged with probiotic strains consortia before (Arm 1—consortium 1) and after (Arm 2—consortium 2) the inoculation with virus as shown in FIG. 19.

Determination of Viral titers in nasal wash: From day 1 through day 42, Arm 1 ferrets received a daily oral gavage of consortium 1 or Placebo. From day 21 to 42, Arm 2 ferrets received a daily oral gavage of consortium 2. The consortia were identical to those used in Example 2. On day 22 ferrets were anesthetized with Ketamine/Xylazine and inoculated with $10^5$ PFU 2019 Novel Coronavirus, Isolate USA-WA1/2020 (SARS-CoV-2). On different days post-infection nasal washes were collected, and viral load was determined of by RT-qPCR as described previously and reported as number of genomes/0 of nasal wash.

Figure 2A:
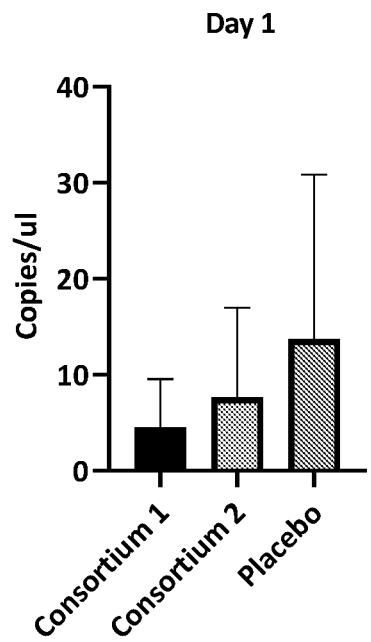
FIG. 2A is a chart showing nasal wash viral titers in SARS CoV-2-infected ferrets on day 1 post infection.
Figure 2B:
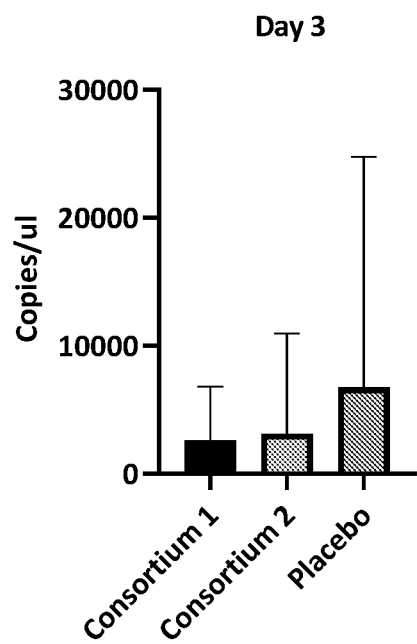
FIG. 2B is a chart showing nasal wash viral titers in SARS CoV-2-infected ferrets on day 3 post infection.

As shown in FIG. 2A and FIG. 2B, administration of consortia 1 and 2 brought about a reduction of viral load by more than 50% on days 1 and 3.

Example 4: Human-Derived Dendritic and Macrophage Cell Stimulation by Probiotics This Example shows probiotic bacteria tested in a human blood derived dendritic and macrophage cell model.

Bacteria: Probiotic strains (DGCC, Danisco Global Culture collection, Niebüll, Germany) were grown to logarithmic growth phase, collected by centrifugation, washed once with PBS and suspended to cell culture medium. The OD600 was adjusted to correspond to bacteria:host cell ratio of 10:1. The bacteria in the consortium 1 (combo1) or consortium 2 (combo 2) were applied on cells in equal proportions. The consortia were identical to those used in Example 2.

Monocyte purification and differentiation to macrophages and dendritic cell: Monocytes were purified from freshly collected leukocyte-rich buffy coats obtained from healthy blood donors. Human peripheral blood mononuclear cells are isolated by density gradient centrifugation followed by purification of monocytes with CD14+ magnetic beads. To obtain macrophages purified monocytes are were plated on 24 well plates $3 \times 10^5$ cells/well and cultured for 7 days in Macrophage-SFM (Gibco, Life Technologies, Grand Island, NY, USA) with recombinant human GM-CSF (Miltenyi Biotech) 1000 IU/ml and 1% Antibiotic-Antimycotic. To differentiate monocytes into immature dendritic cells, monocytes were plated on 12 well plates $5 \times 10^5$ cells/well (Falcon, Corning, NY, USA) and cultured for 7 d in RPMI-1640 (Sigma) supplemented with 1% Antibiotic-Antimycotic, 10% fetal bovine serum (FBS), IL-4 (400 IU/ml) and GM-CSF (1000 IU/ml).

Stimulation of Immune Cells: Cells from six four blood donors were stimulated with probiotic bacteria consortia alone (bacteria:cell ratio of 10:1) or in combination with TLR ligand blend, Poly I:C, 30 µg/ml+R848, 10 µM (both from Sigma-Aldrich, St. Louis, MO, USA) for 24 h. PBMCs without stimulation were used as a control, DMSO were used as a control for PolyI:C+R848 containing treatments.

ELISA analysis: Cell culture supernatants from macrophage and dendritic cell cultures are analyzed for IFN-γ, IL-1β, IL-6, IL-10, IL-12p70, and TNF-α by Quanterix Human 6-Plex Ciraplex Array (Quanterix, Inc., Billerica, MA, USA). In addition, dendritic cell supernatants were analyzed for IL-23 and TGF-β by Quanterix Human 1-plex Assays according to manufacturer's instructions. Results were analyzed with CiraSoft software (Quanterix).

Figure 3:
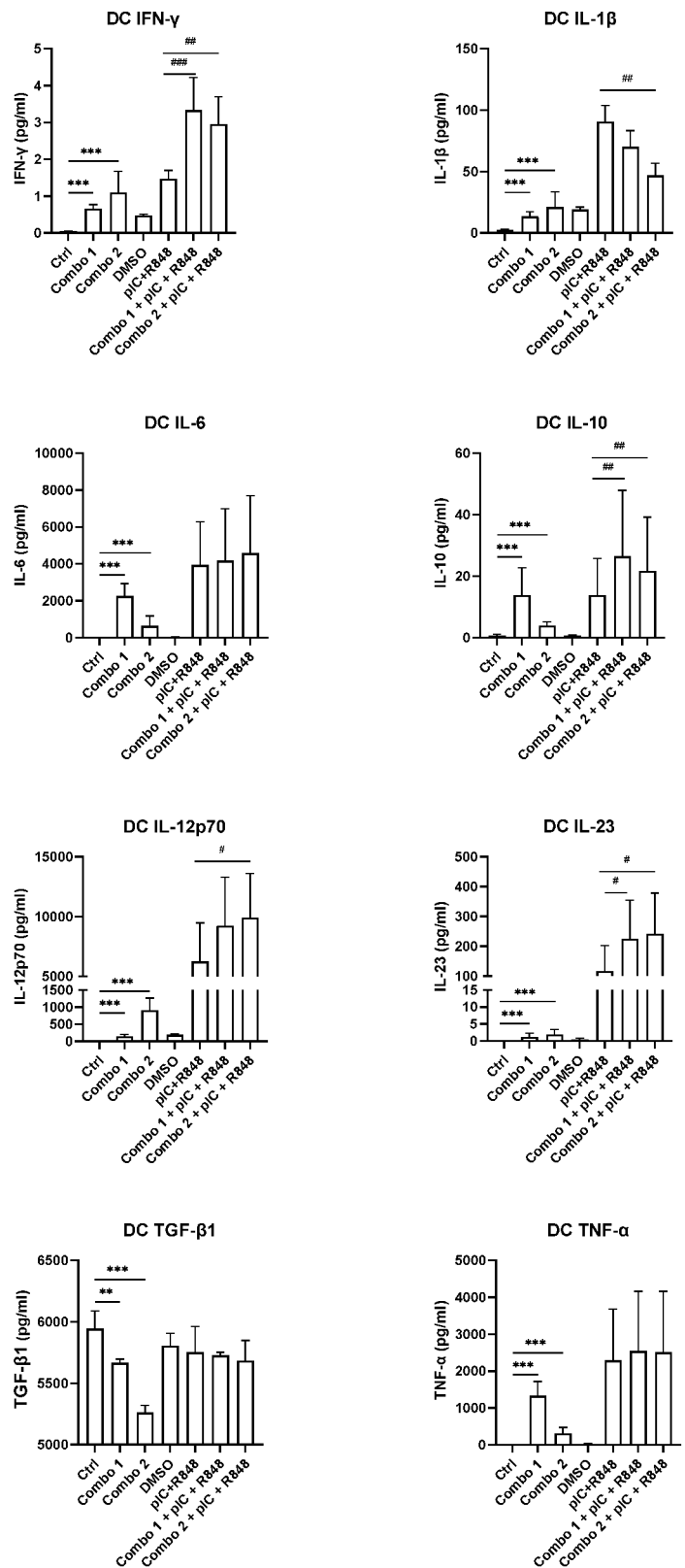
FIG. 3 depicts a series of graphs showing the effect of bacterial consortia on dendritic cell (DC) cytokine production. $*p=0.01=<0.05$; $p=0.001=<0.01$; $*p<0.001$ vs ctrl and $\#p=0.01=<0.05$; $\#\#p=0.001=<0.01$; $\#\#\#p<0.001$ vs pIC+R848.

As shown in FIG. 3, treatment of dendritic cells with bacterial consortia Combo1 and Combo 2 influence significantly the production of all cytokines versus the untreated dendritic cells (Ctrl). Combo1 and Combo 2 with pIC+R848 influences significantly the production of several cytokines versus pIC+R848 alone. *p=0.01=<0.05; p=0.001=<0.01; *p<0.001 vs ctrl and #p=0.01=<0.05; ##p=0.001=<0.01; ###p<0.001 vs pIC+R848. The data was analyzed with linear model using change from a baseline (ctrl or pIC+R848) as response.

Combo 1 and Combo 2 increase production of IL-12 and IFNγ that are critical for Th1 responses against viruses as well as stimulate IL-10 production that controls inflammatory response. Also evident is decrease in TGF-β and increase in IL-23 suggesting some Th17 polarization by the combinations. The combinations do not increase the production of inflammatory cytokine TNF-α, or IL-6 and IL-1β, associated with inflammatory and Th17 response. Thus, both combinations appear to drive Th1 polarization with IL-10 production.

Figure 4:
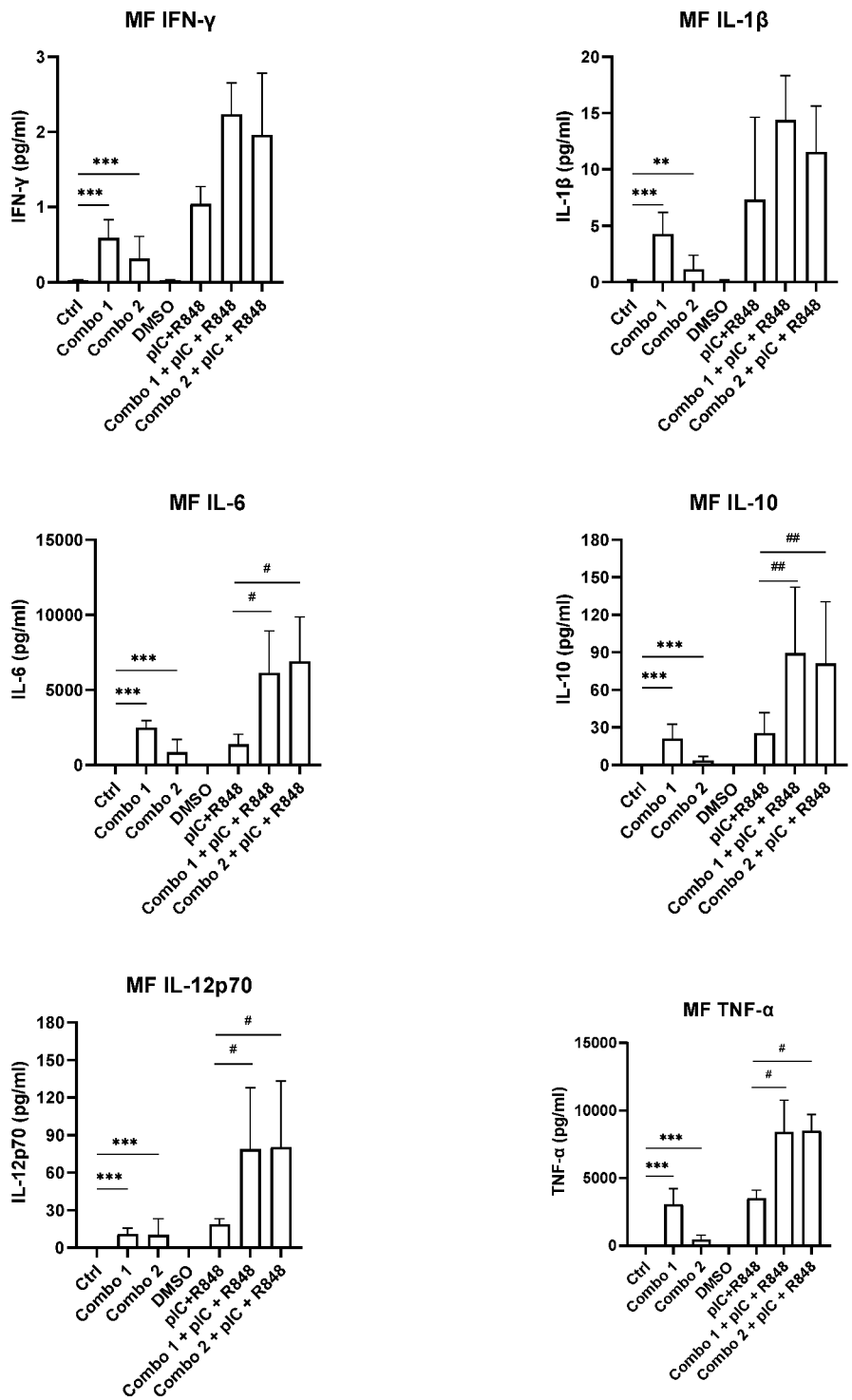
FIG. 4 depicts a series of graphs showing the effect of bacterial consortia on macrophage (MF) cytokine production. *p=0.01=<0.05; p=0.001=<0.01; *p<0.001 vs ctrl and #p=0.01=<0.05; ##p=0.001=<0.01; ###p<0.001 vs pIC+R848.
Figure 5:
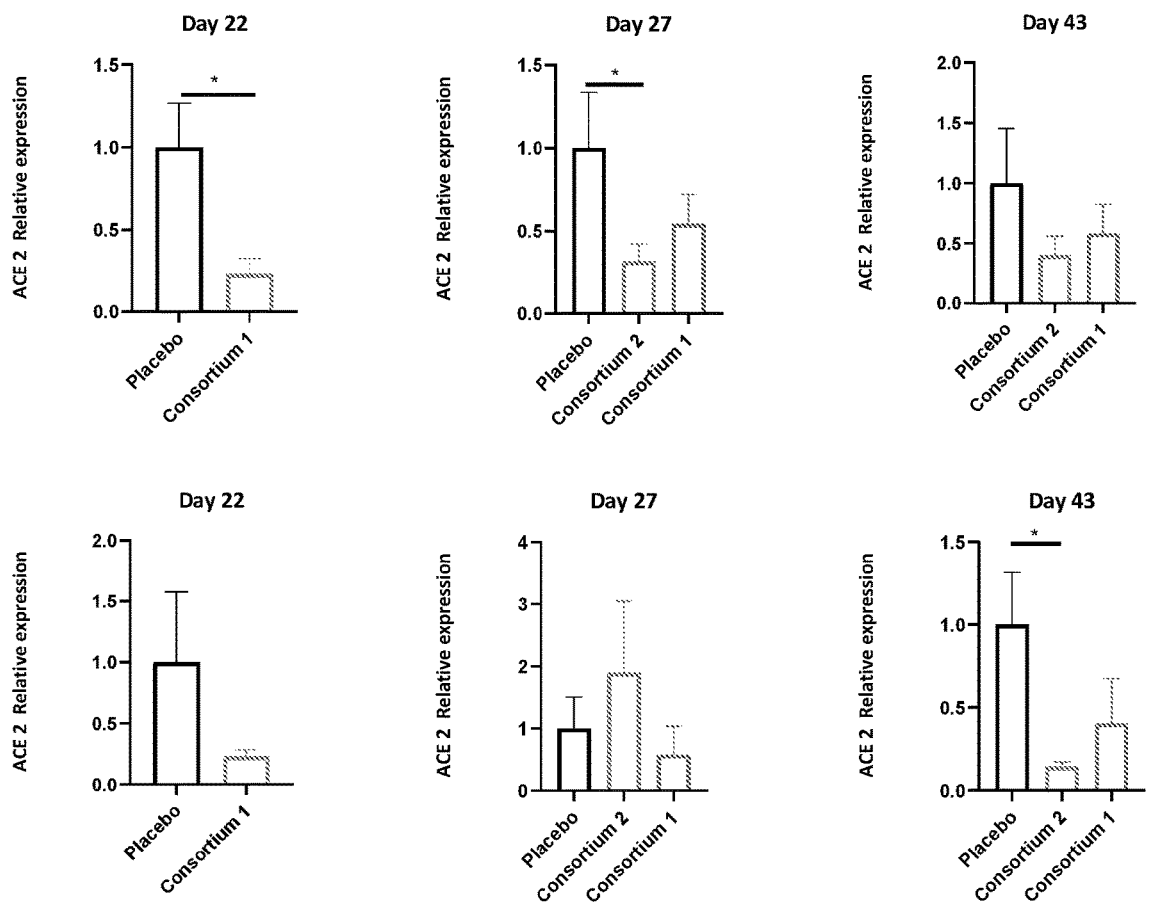
FIG. 5 depicts a series of graphs showing modulation in the expression of ACE 2 in ferrets by probiotic consortia.
Figure 6:
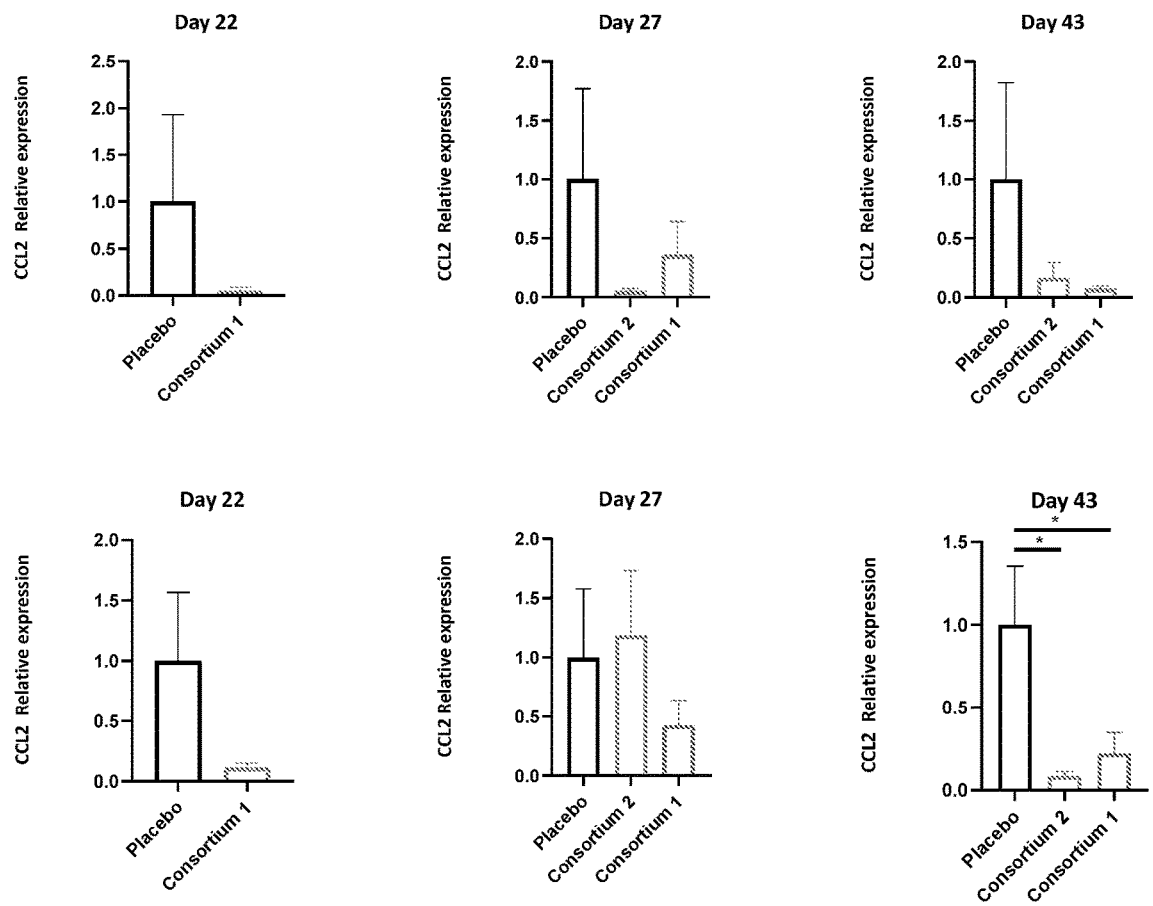
FIG. 6 depicts a series of graphs showing modulation in the expression of CCL2 in ferrets by probiotic consortia.
Figure 7:
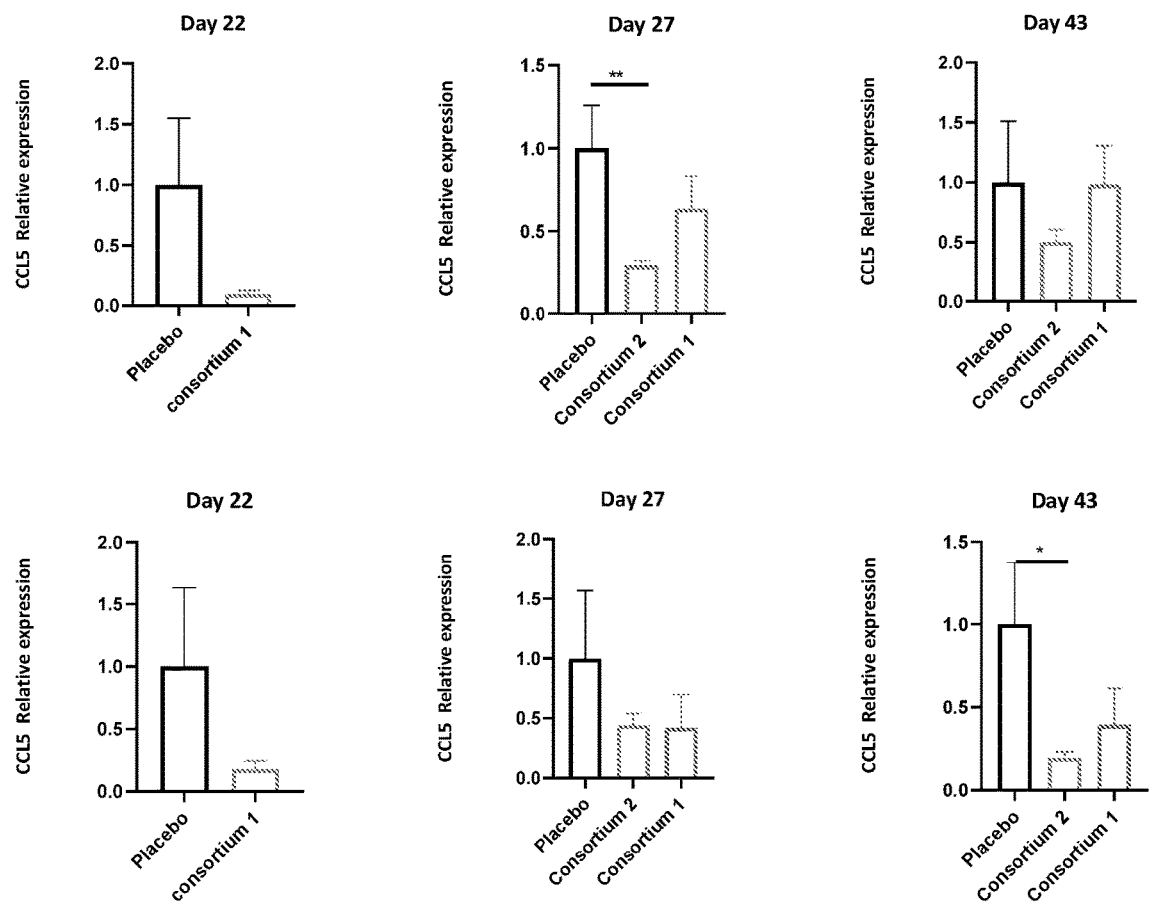
FIG. 7 depicts a series of graphs showing modulation in the expression of CCL2 in ferrets by probiotic consortia.
Figure 8:
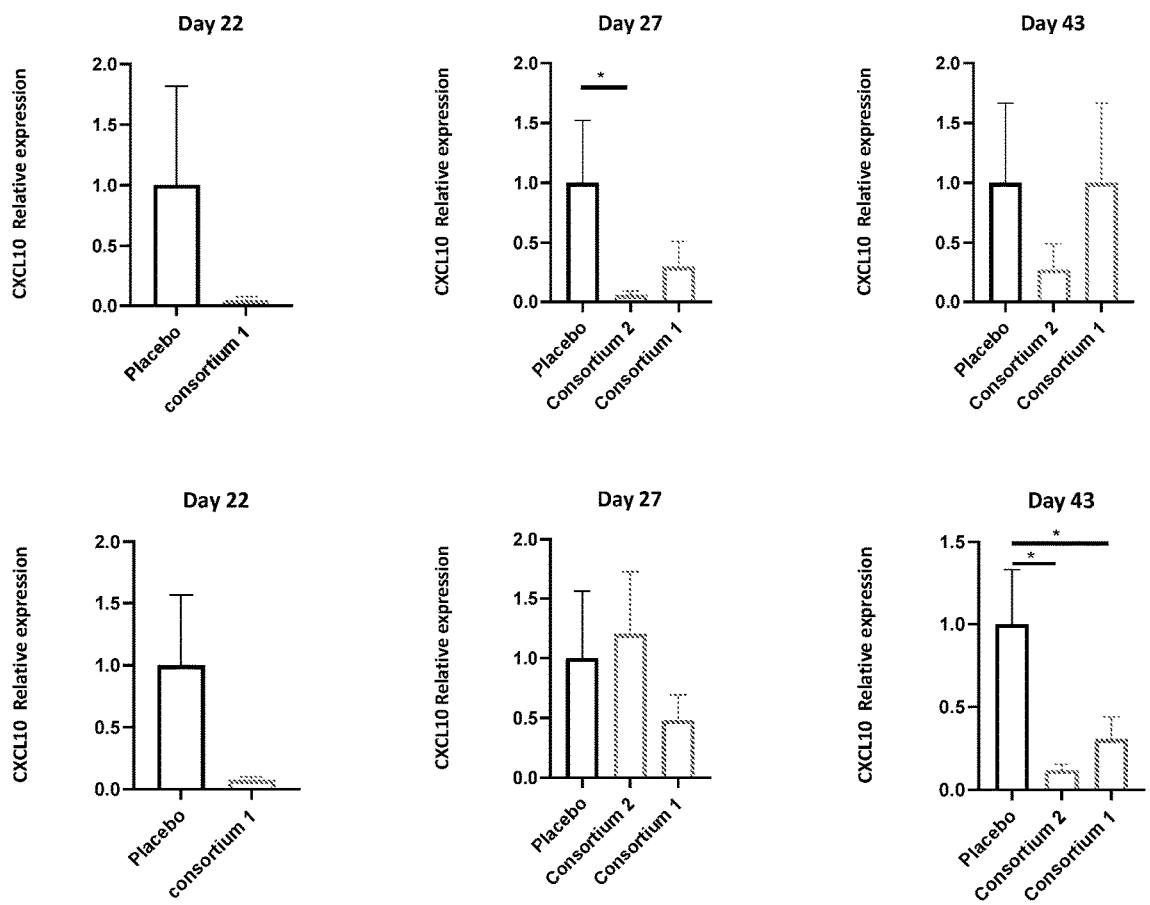
FIG. 8 depicts a series of graphs showing modulation in the expression of CCL2 in ferrets by probiotic consortia.
Figure 9:
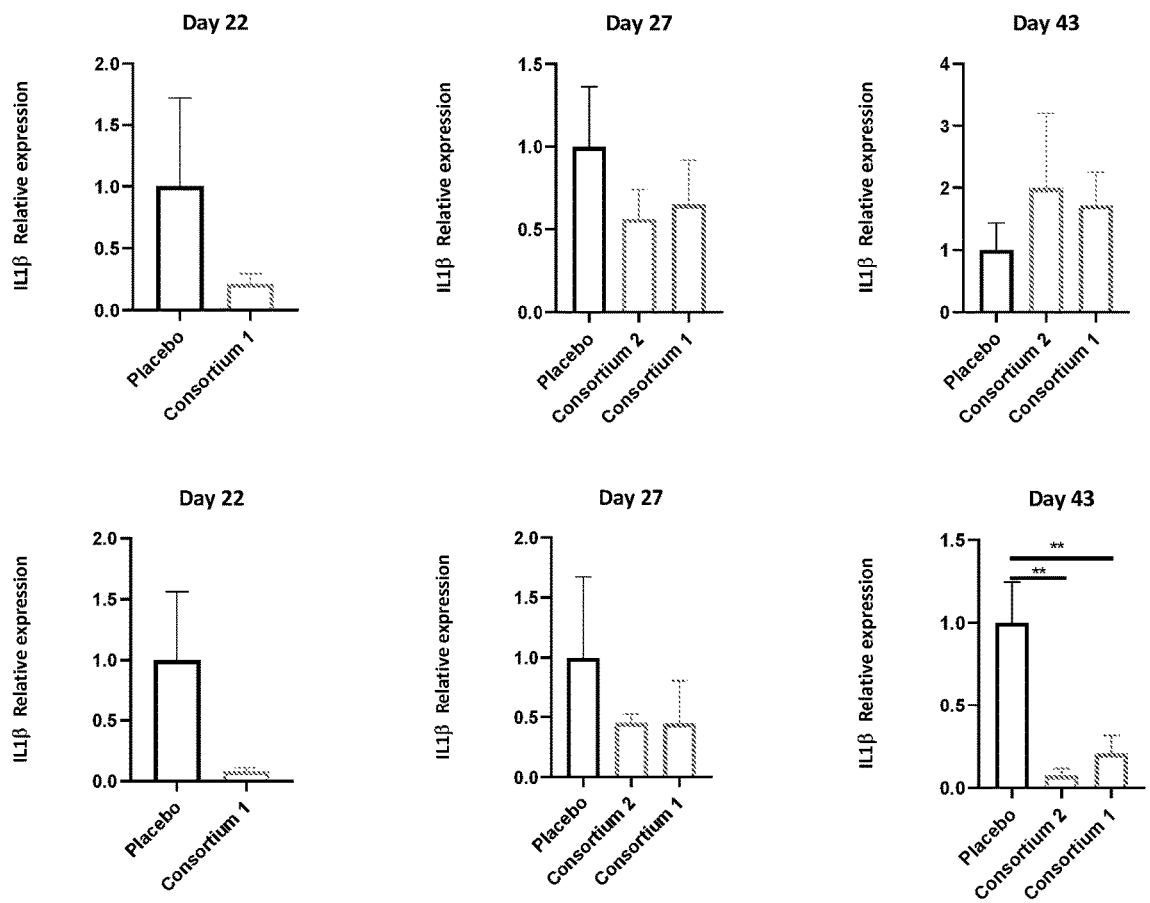
FIG. 9 depicts a series of graphs showing modulation in the expression of CCL2 in ferrets by probiotic consortia.
Figure 10:
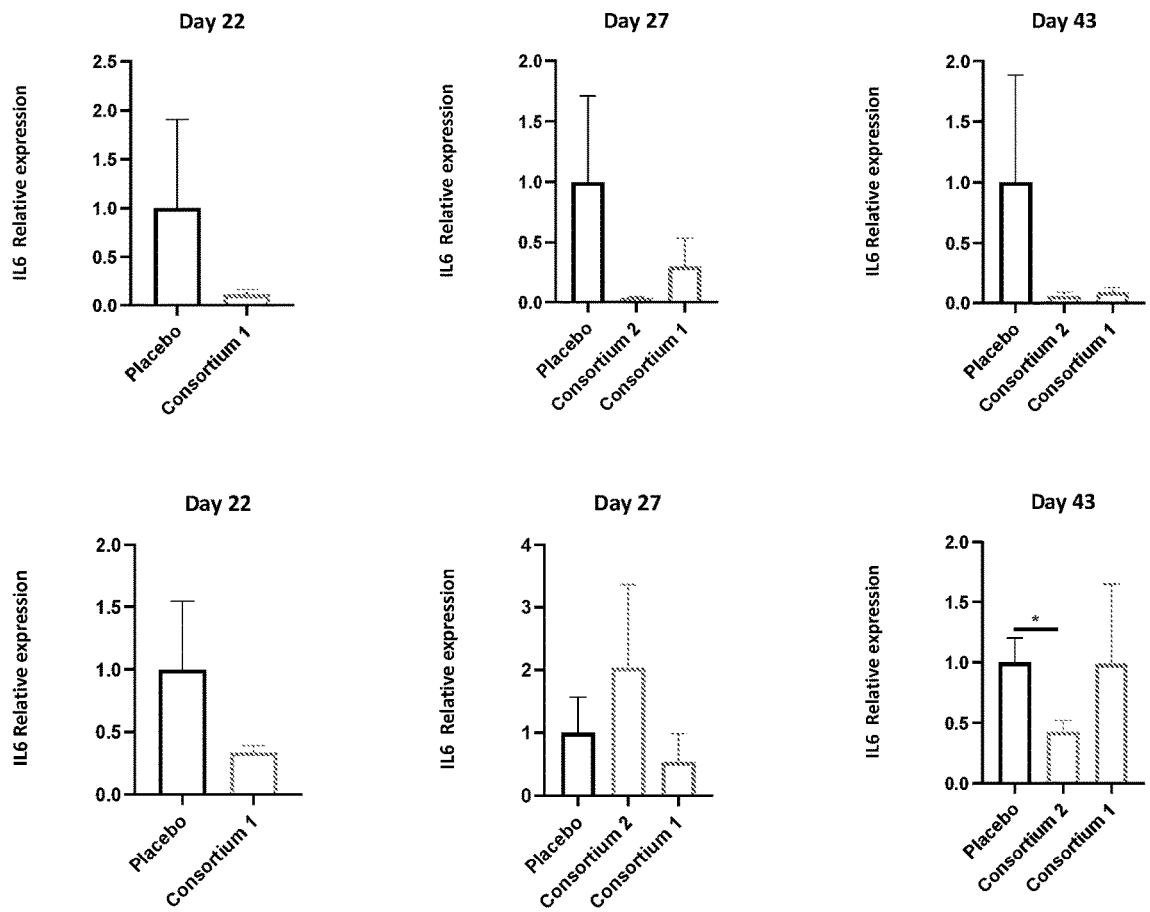
FIG. 10 depicts a series of graphs showing modulation in the expression of IL6 in ferrets by probiotic consortia.
Figure 11:
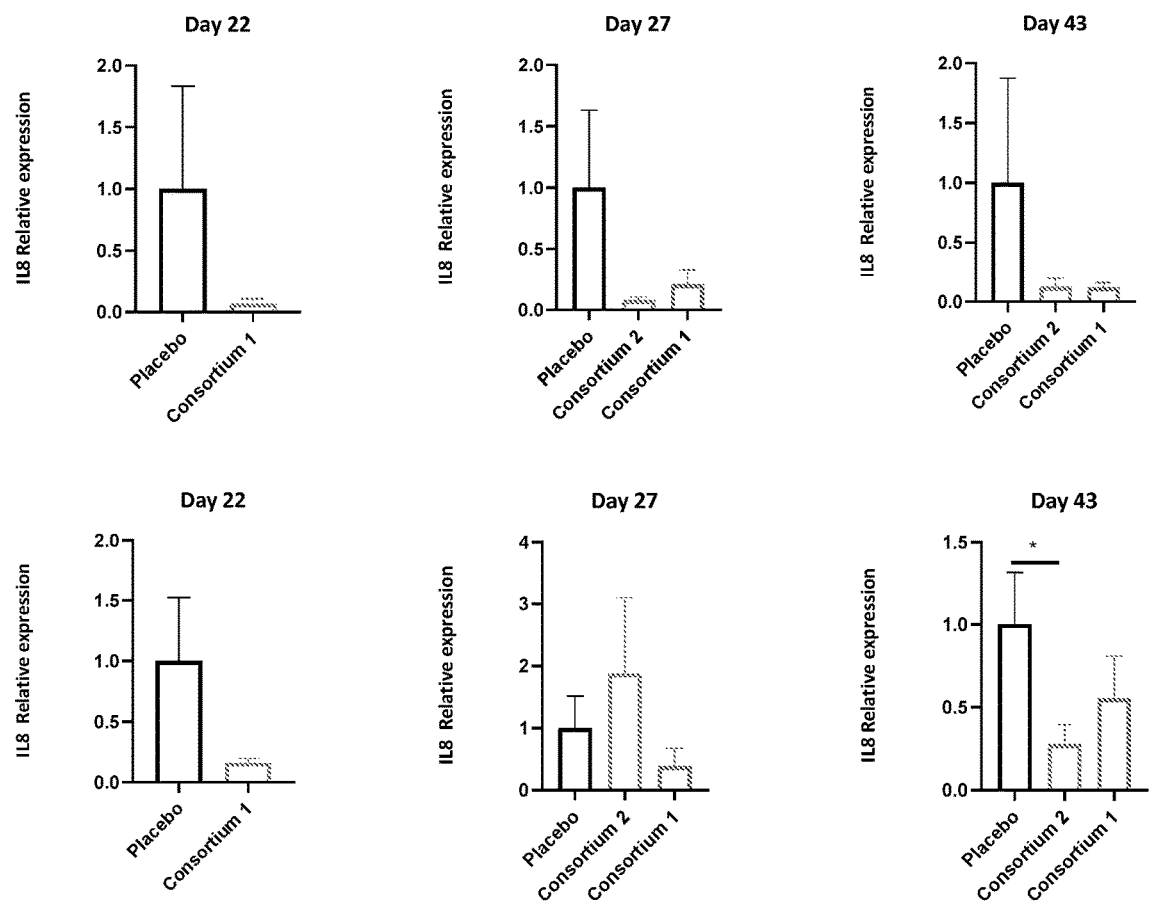
FIG. 11 depicts a series of graphs showing modulation in the expression of IL6 in ferrets by probiotic consortia.
Figure 12:
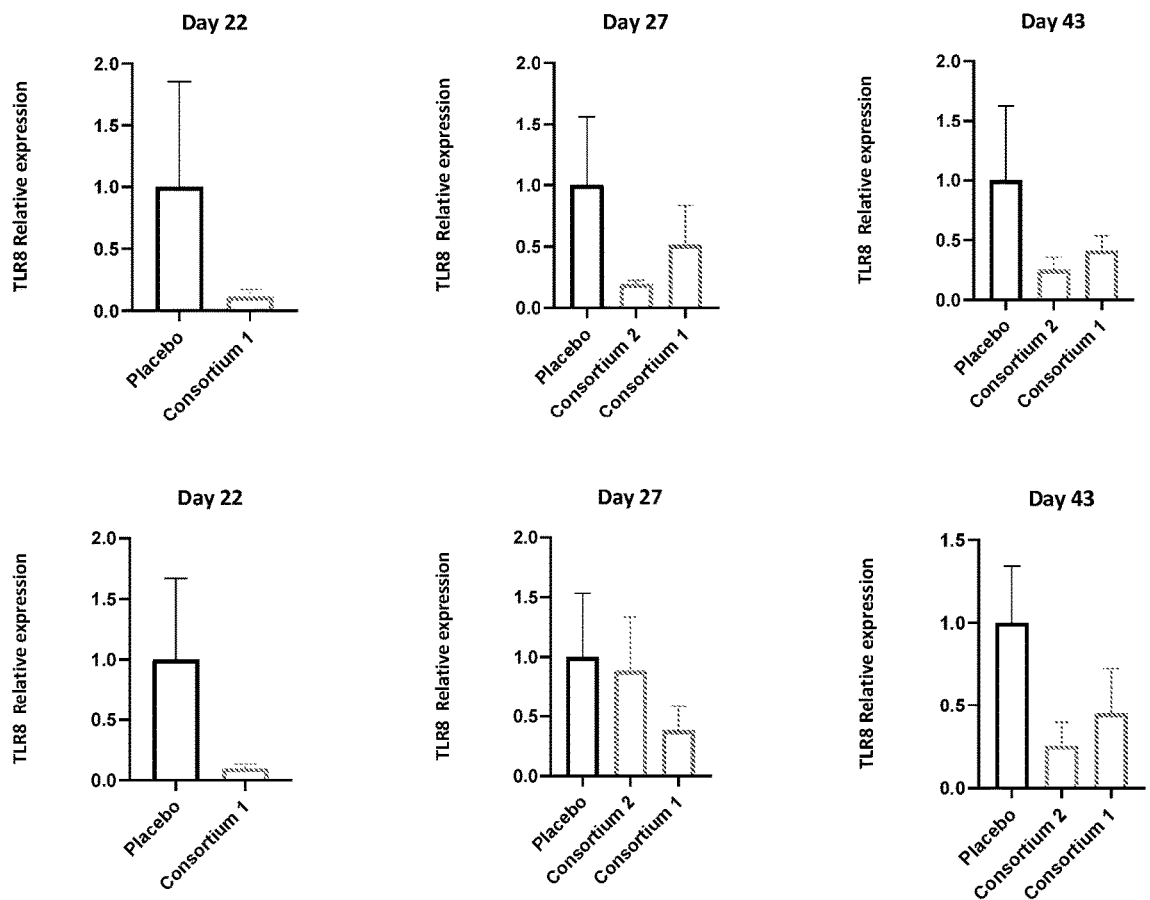
FIG. 12 depicts a series of graphs showing modulation in the expression of TLR 8 in ferrets by probiotic consortia.
Figure 13:
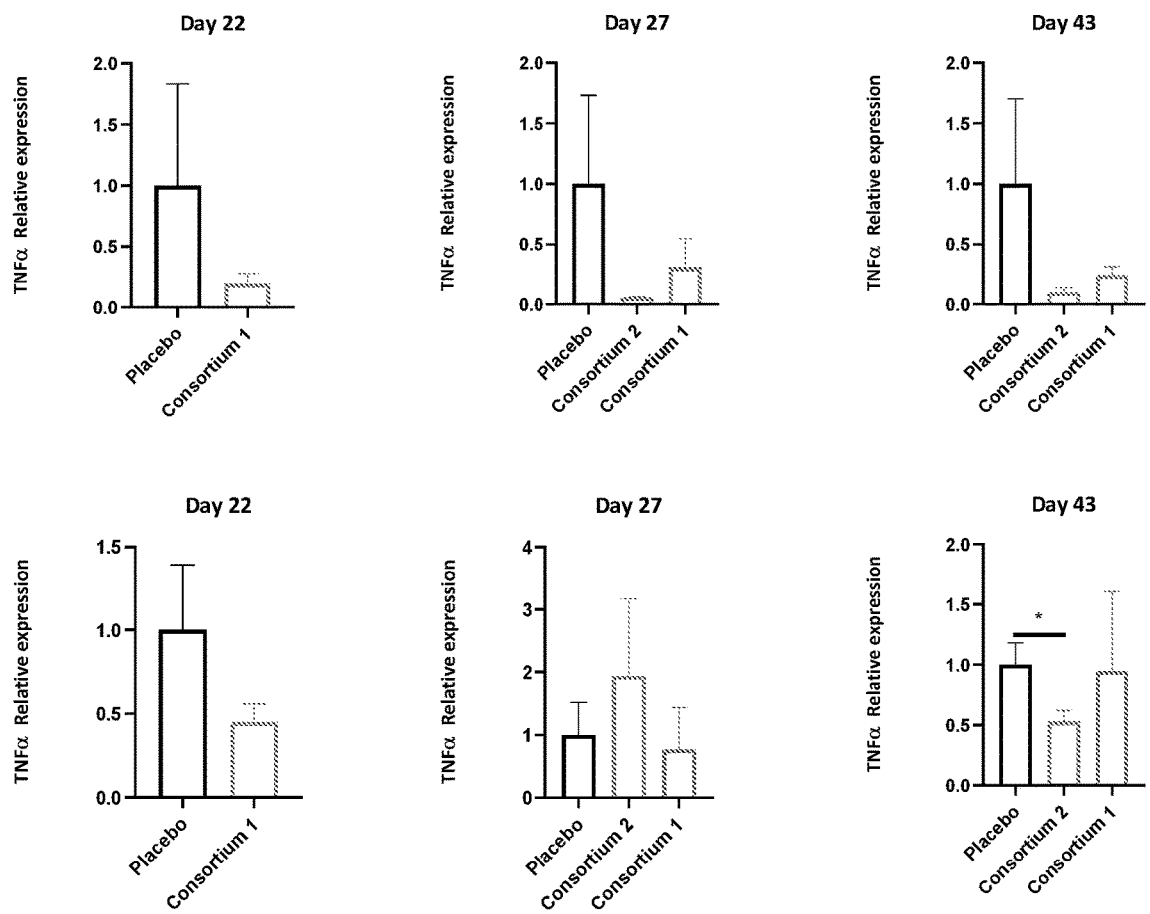
FIG. 13 depicts a series of graphs showing modulation in the expression of TLR 8 in ferrets by probiotic consortia.
Figure 14:
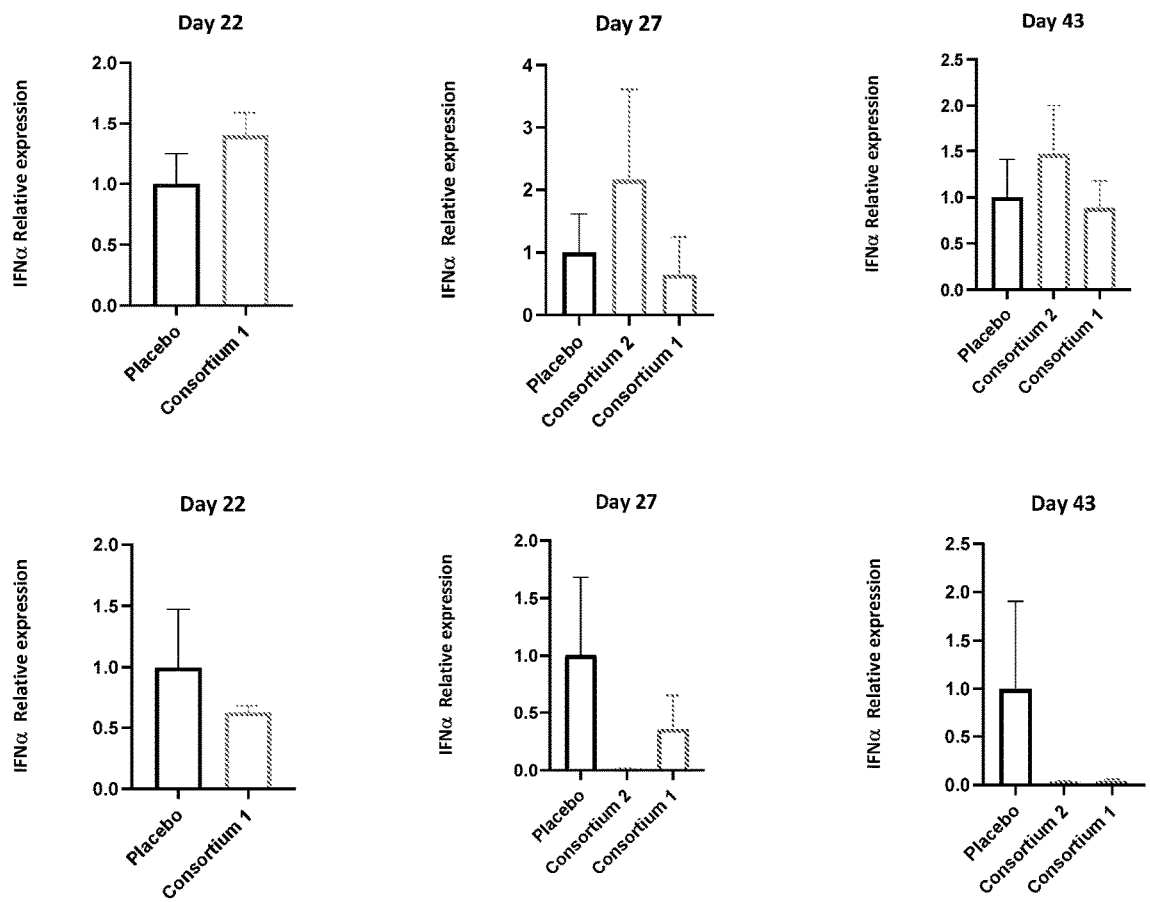
FIG. 14 depicts a series of graphs showing modulation in the expression of IFNα in ferrets by probiotic consortia.
Figure 15:
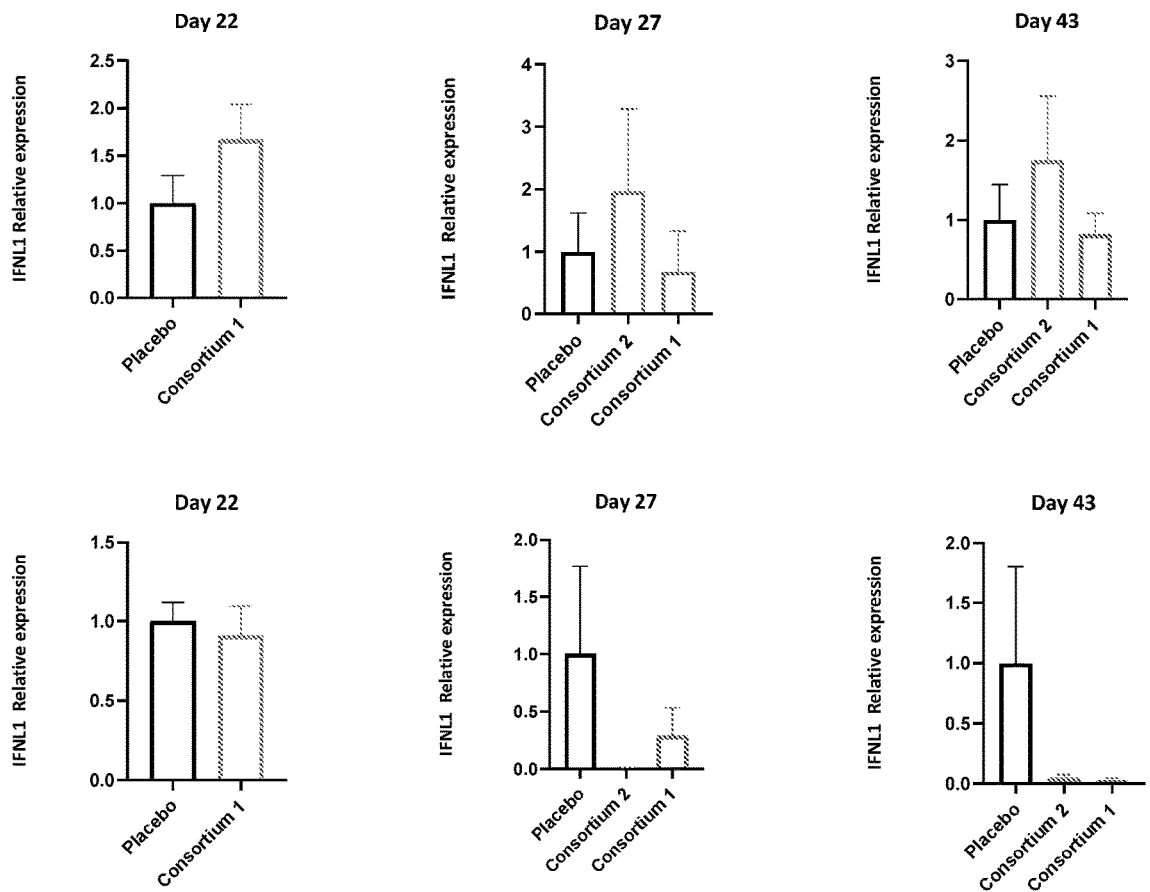
FIG. 15 depicts a series of graphs showing modulation in the expression of IFNL1 in ferrets by probiotic consortia.
Figure 16:
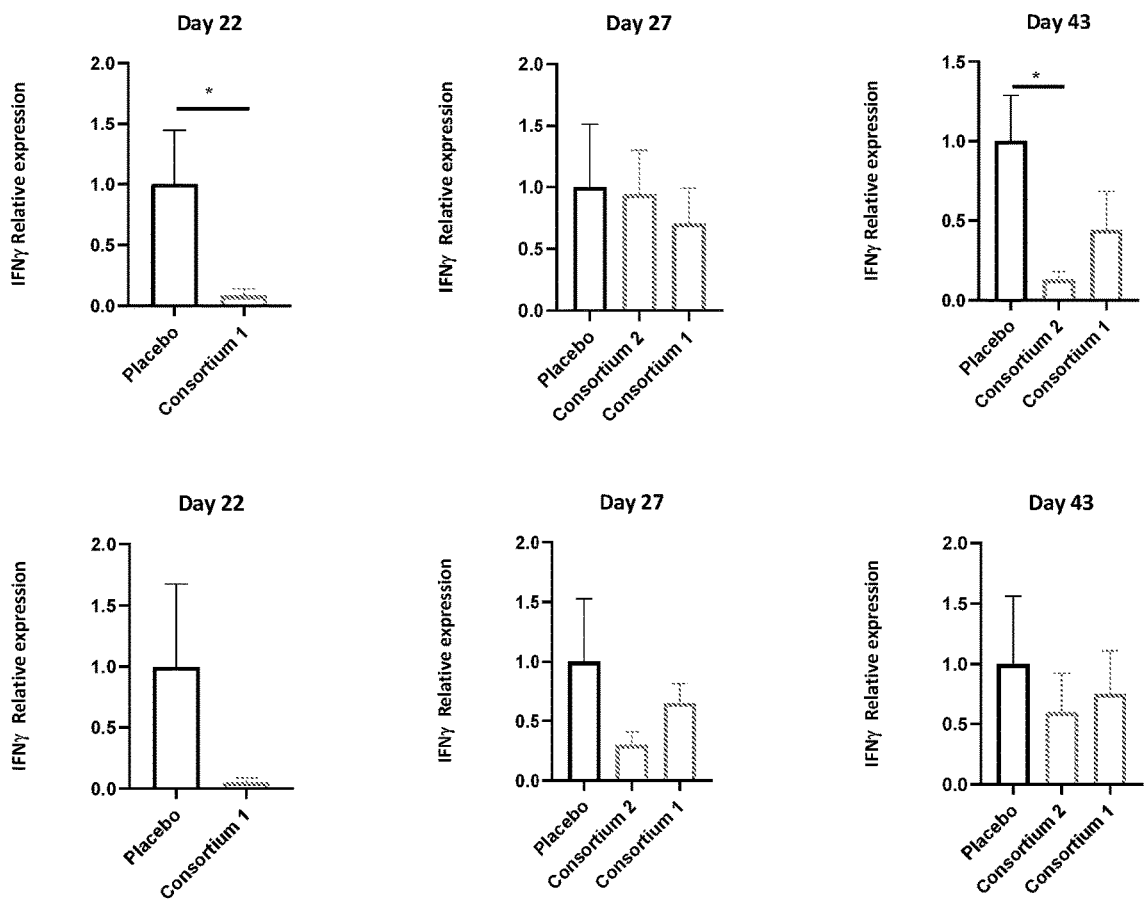
FIG. 16 depicts a series of graphs showing modulation in the expression of IFNγ in ferrets by probiotic consortia.
Figure 17:
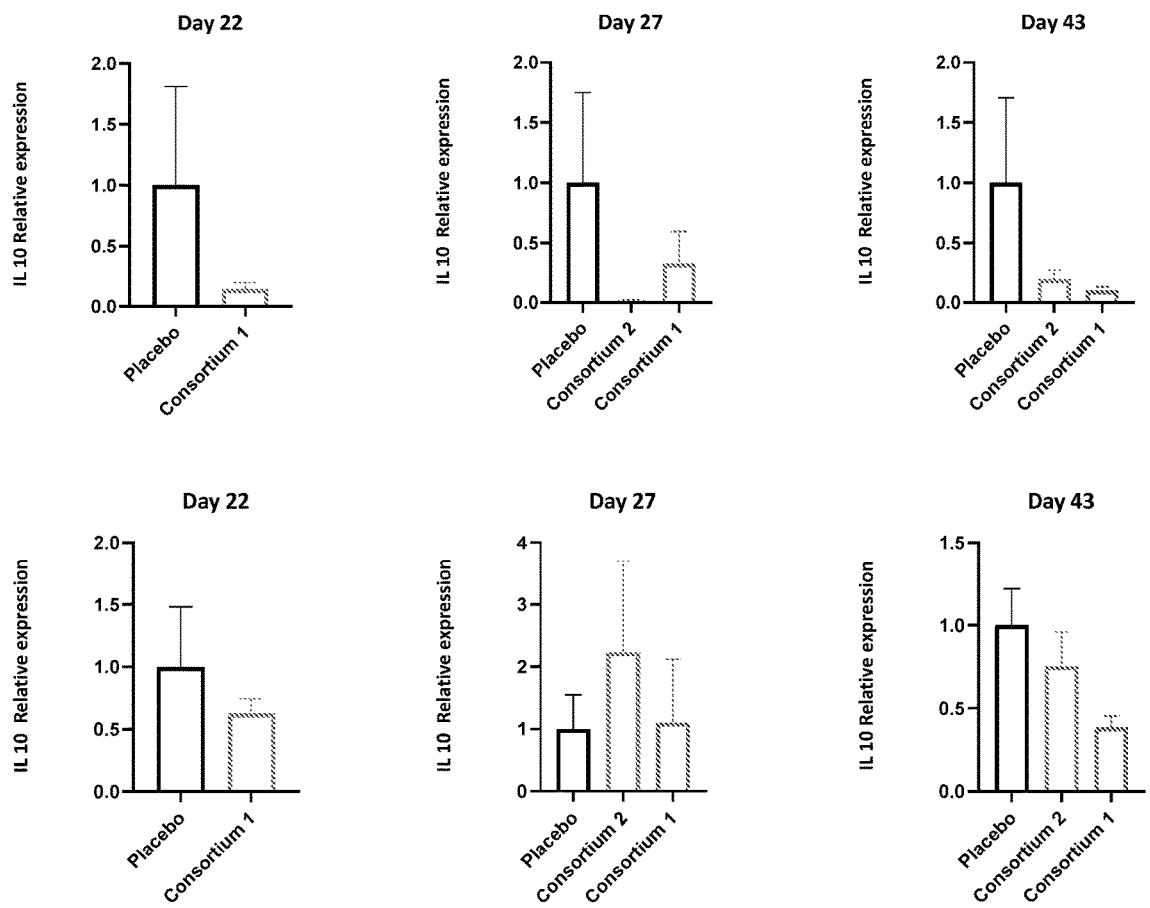
FIG. 17 depicts a series of graphs showing modulation in the expression of IFNγ in ferrets by probiotic consortia.

As shown in FIG. 4, treatment of macrophages with Combo1 and Combo 2 influence significantly the production of all cytokines versus the untreated dendritic cells (Ctrl). Combo1 and Combo 2 with pIC+R848 influence significantly the production of several cytokines versus pIC+R848 alone. *p=0.01=<0.05; p=0.001=<0.01; *p<0.001 vs ctrl and #p=0.01=<0.05; ##p=0.001=<0.01; ###p<0.001 vs pIC+R848. The data was analyzed with linear model using change from a baseline (ctrl or pIC+R848) as response.

Combo 1 and Combo 2 increase production of IL-12 that is critical for initiating Th1 responses against viruses as well as stimulate IL-10 production that controls inflammatory response. The combinations have an impact on IL-6 that associates with driving antibody production and acute inflammatory response. In combination with pIC+R848, the combinations do not significantly increase production of inflammatory cytokines IFN-γ or IL-10.

Example 5: Ferret-Derived Dendritic and Macrophage Cell Stimulation by Probiotics This Example determined changes in cytokine, chemokine, and receptor proteins in ferrets following administration of probiotics derived from the SARS CoV-2-infected animals described in Example 2.

Gene expression analysis: Lung and duodenum were collected and stored in trizol. Tissue RNA was isolated using Direct-Zol RNA Miniprep Plus kit. Two step RT qPCR were used to analyze the gene expression in ferret lung and duodenum total RNA samples. Reverse transcription was performed with iScript Reverse Transcribe Supermix (Bio-Rad). Briefly, 1 µg total lung RNA or 0.5 µg total duodenum RNA was used for reverse transcription. The total RT reaction volume was 40 µL and RT was performed in a 96 well plate on a Bio-Rad CFX96 Touch Real Time PCR Detection System. After RT, the cDNA was diluted with nuclease free water to bring the final total volume up to 200 µL (5× dilution). 5 µL of diluted cDNA was used for qPCR analysis of the expression of gene of interest. The total PCR reaction volume was 15 µL per well (10 µL master mix+5 µL cDNA sample) and the qPCR was performed on the CFX384 Touch Real-Time PCR Detection System (Bio-Rad) using the cycling conditions listed below:

| Temperature | Time | Cycle(s) |
| --- | --- | --- |
| 95° C. | 2 minutes | 1 |
| 95° C. | 10 seconds | 40 |

*60° C. or 62° C. 45 seconds
*60° C. for CCL2, IFNα, IFNL1 and IL8 62 °C for all other genes (CCL5, CXCL10, IFNγ, IL10, IL1β, IL6, TLR8, TNFα, ACE2 and RPS18)

Each plate contains a positive control (prepared from stimulated ferret PBMC cells) in duplicate wells, an NTC in duplicate wells and all test samples in duplicate wells.

Calculation, Data Analysis and Presentation: The threshold baseline of the qPCR assay was manually set at 200 for all plates if the automatically calculated (by the CFX Maestro 1.1 software) threshold baseline was >200. The 200-threshold baseline value was determined at the development/qualification stage of RT-qPCR assays of genes of interest. However, if the automatically calculated threshold baseline was <200, then the threshold baseline was directly used. Cq value in each well was also automatically calculated by the Maestro 1.1 software based on the threshold baseline. Data generated by the software were exported to a Microsoft Excel (Microsoft Corporation; Redmond, WA) spreadsheet for data processing.

Relative gene expression was calculated using the following formula:

$$2-(\Delta Cq), \text{ where } \Delta Cq \text{ is } Cq(\text{each sample})-Cq(\text{day 1 mean})$$

The results were normalized to Day 1 basal gene expression level. After the relative expression value is calculated for each sample, the value was further adjusted to RNA amount if a different RNA amount was used for RT. In addition, data with further normalizations to the placebo on each day are also presented. The relative expression of each treatment group was compared with corresponding placebo group and the p value was calculated using Student's t-test (one-tailed distribution, two sample equal variance). Difference between means were considered to be significant at $p<0.05$.

As shown in FIGS. 5-17, analysis in lung and duodenum tissue samples demonstrated that IFNα, IFNL1, and TLR8 were not regulated by the any treatments, but other genes (ACE2, CCL2, IL10, CCL5, CXCL10, IFNγ, IL1β, IL6, IL8, TNFα) were downregulated in lung or duodenum either on specific day(s) or in treatment group(s), among them CCL2, CXCL10 and IL1β were downregulated in lungs in both prevention and treatment groups (vs. placebo) on day 43. These results suggest that the test article (probiotics) could affect cytokine expressions in different organs in a ferret model under the experimental conditions of viral infection with SARS COv-2.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for decreasing viral load in a subject infected with SARS-CoV2 coronavirus, said method comprising administering an effective amount of a composition comprising *Bifidobacterium longum* subsp. *infantis* strain Bi-26; *Bifidobacterium animalis* subsp. *lactis* strain Bl-04; *Lacticaseibacillus paracasei* strain Lpc-37; *Lacticaseibacillus rhamnosus* strain Lr-32 and/or *Ligilactobacillus salivarius* strain Ls-33 to said subject infected with SARS-CoV2 coronavirus, wherein the viral load is decreased relative to the viral load in a subject that has not been treated with an effective amount of the composition.

2. The method according to claim 1, wherein the subject has one or more pre-existing conditions selected from the group consisting of obesity, type II diabetes, chronic lung disease or moderate to severe asthma, heart conditions, immunocompromised, chronic kidney disease and liver disease.

3. The method according to claim 1, wherein the subject is 65 years of age or older and/or is a resident in a nursing home or long-term care facility or jail or prison.

* * * * *